United States Patent
Yunoki et al.

(10) Patent No.: US 11,753,462 B2
(45) Date of Patent: Sep. 12, 2023

(54) HIGHLY ORIENTED COLLAGEN FIBRIL BUNDLE AND METHOD OF PRODUCING SAME

(71) Applicant: Tokyo Metropolitan Industrial Technology Research Institute, Tokyo (JP)

(72) Inventors: Shunji Yunoki, Tokyo (JP); Mizue Ebisawa, Tokyo (JP); Eiji Kondo, Hokkaido (JP); Kazunori Yasuda, Hokkaido (JP)

(73) Assignee: Tokyo Metropolitan Industrial Technology Research Institute, Tokyo (JP)

( * ) Notice: Subject to any disclaimer, the term of this patent is extended or adjusted under 35 U.S.C. 154(b) by 468 days.

(21) Appl. No.: 16/762,183

(22) PCT Filed: Nov. 5, 2018

(86) PCT No.: PCT/JP2018/041057
§ 371 (c)(1),
(2) Date: May 7, 2020

(87) PCT Pub. No.: WO2019/093280
PCT Pub. Date: May 16, 2019

(65) Prior Publication Data
US 2020/0354432 A1    Nov. 12, 2020

(30) Foreign Application Priority Data

Nov. 8, 2017  (JP) .................................. 2017-215184

(51) Int. Cl.
*C07K 14/78* (2006.01)
*D01F 4/00* (2006.01)

(52) U.S. Cl.
CPC ................ *C07K 14/78* (2013.01); *D01F 4/00* (2013.01)

(58) Field of Classification Search
None
See application file for complete search history.

(56) References Cited

FOREIGN PATENT DOCUMENTS

| JP | 2006280222 A | 10/2006 |
|----|--------------|---------|
| JP | 2016280222 A | 10/2006 |
| JP | 2016-69783 | * 5/2016 |
| JP | 2016-77411 | * 5/2016 |
| JP | 2016069783 A | 5/2016 |
| JP | 2016077411 A | 5/2016 |
| JP | 2017-61757 | * 3/2017 |
| JP | 2017061757 A | 3/2017 |
| WO | 2010101639 A | 9/2010 |

OTHER PUBLICATIONS

Yunoki et al.,"Anovelfabricationmethodtocreateathickcollagenbund lecomposedofuniaxiallyalignedfibrils: An essentialtechnologyforthedevelopmentof . . . ",Feb. 26, 2015,pp. 3054-3065,vol. 103A,Publisher:J BiomedMaterResPartA.*
Hatayama, Hiroya et al.,"Conditionsforproductionof orientedcollagenfibergelusingshear stress", ResearchreportsoftheTokyoMetropolitan Industrial Technology Research Institute.*
Cheng et al., "An electrochemical fabrication process for the assembly of anisotropically oriented collagen bundles", Aug. 2008, pp. 3278-3288, vol. 29, No. 22, Publisher: Biomaterials.
Hatayama et al., "Required conditions for the fabrication of collagen gels comprising aligned collagen fibrils using shear stress", 2016, pp. 22-26, No. 11, Publisher: Bulletin of TIRI.
Lanfer et al., "Aligned fibrillar collagen matrices obtained by shear flow deposition", Oct. 2008, pp. 3888-3895, vol. 29, No. 28, Publisher: Biomaterials.
Pins et al., "Self-assembly of collagen fibers. Influence of fibrillar alignment and decorin on mechanical properties", Oct. 1997, pp. 2164-2172, vol. 73, No. 4, Publisher: Biophys J.
Saeidi, et al., "Production of highly aligned collagen lamellae by combining shear force and thin film confinement", Jun. 2011, pp. 2437-2447, vol. 7, No. 6, Publisher: Acta Biomaterialia.
Younesi et al., "Fabrication of Compositionally and Topographically Complex Robust Tissue Forms by 3D-Electrochemical Compaction of Collagen", Sep. 2015, pp. 035001, vol. 7, No. 3, Publisher: Biofabrication.
International Search Report received in PCT/JP2018/041057 dated Jan. 29, 2019.
Written Opinion received in PCT/JP2018/041057 dated Jan. 29, 2019.

* cited by examiner

*Primary Examiner* — Maury A Audet
(74) *Attorney, Agent, or Firm* — Suzannah K. Sundby, Esq.; Canady + Lortz LLP

(57) ABSTRACT

The present invention relates to a highly oriented collagen fibril bundle having a length in a major axis direction of 1 m or more.

13 Claims, 14 Drawing Sheets

HIGHLY ORIENTED COLLAGEN FIBRIL BUNDLE AND METHOD OF PRODUCING SAME

TECHNICAL FIELD

The present invention relates to a widely and highly oriented collagen fibril bundle or a collagen gel containing the same, and a method of producing the same.

BACKGROUND ART

In the fields of tissue engineering, the development of medical scaffolding materials that imitate biological structures by orienting cell scaffold molecules such as collagen has been actively performed.

In the related art, since there has been no molded component of collagen fibrillar gel that satisfied the following conditions, there have been problems in that it was not possible to produce collagen fibrils beneficial for the development of artificial tendons, the development of coating materials such as collagen membranes and sponge molded components with enhanced strength, and the development of materials for joint surgery according to conversion into a woven fabric.
1) A thick molded component of collagen fibrillar gel or a thick band-like molded component of collagen fibrillar gel in which collagen fibrils have a high orientation.
2) A molded component of collagen fibrillar gel with crosslinked collagen which satisfies the condition 1).
3) Thick collagen fibrils obtained from the string-like molded component 1) or 2).
4) A thick collagen sheet obtained from the band-like gel molded component 1) or 2).

In addition, in order to industrialize the above molded components of collagen fibrillar gel, a molding technique in which all of the following conditions are satisfied is necessary, but it has not been developed yet.
a) Continuous spinning of medical collagens is possible.
b) Collagen fibrils are oriented uniaxially.
c) The diameter of a string-like collagen gel can be controlled to be in a range of 1 mm to 10 mm.
d) Continuous gel molding with various shapes can be performed by changing molds.

Regarding collagen orientation techniques, there are methods using a shear stress, a magnetic field, an electric field, and the like (Non-Patent Documents 1 to 4 and Patent Documents 1 to 3). Among these, a molecular orientation technique using a shear stress is thought to be closest to practical use as a method of producing a medical instrument in consideration of mass productivity.

CITATION LIST

Patent Documents

Patent Document 1: Patent Publication JP-A-2016-77411
Patent Document 2: WO 2010/101639
Patent Document 3: Patent Publication JP-A-2006-280222

Non-Patent Documents

Non-Patent Document 1: Saeidi et al. Acta Biomater 7, 2437-47 (2011)
Non-Patent Document 2: Lanfer et al. Biomaterials 29, 3888-95 (2008)
Non-Patent Document 3: Pin et al. Biophysical Journal 73, 2164 (1997)
Non-Patent Document 4: Cheng et al. Biomaterials 29, 3278 (2008)
Non-Patent Document 5: Younesi et al. Advanced Functional Materials 24, 5762 (2014)

SUMMARY

Technical Problem

However, when orienting of collagen fibrils using a shear stress is attempted, there is a problem that it is not possible to prepare highly oriented collagen fibrils of which the length exceeds a predetermined value. For example, in Non-Patent Document 1, a technique for collagen fibrillogenesis under a shear force equivalent to a shear rate of 180 to 2,500 ($s^{-1}$) using a spin coater is disclosed. However, the spin coater is a device for rotating a disk at a high speed, and even if fibrils can be collected from the outer edge using a disk with a maximum diameter ($\varphi$30 cm) of the device used in this technique, the total length of collagen fibrils is only about 94 cm.

In Non-Patent Document 2, a technique in which a dilute collagen solution is passed through a microflow path with a width of 1 mm×a depth of 74 μm, fibrillogenesis is promoted and collagen fibrils are attached to a substrate is disclosed, but the length of the flow path is only 8 mm. When elongation of a collagen fibril molded component is attempted by increasing the length of the microflow path, a uniform laminar flow is formed only up to a limit of several cm from an inlet, and it is difficult to produce a collagen molded component with a length that is equal or longer than the limit by orienting fibrils.

Here, in Patent Document 1, a method of producing a highly oriented collagen gel is described. However, the collagen gel described in Patent Document 1 is produced using a batch type molding technique without using continuous spinning. In addition, in Patent Document 1, a method of applying shear to a collagen aqueous solution using a temperature control type rheometer with a Peltier controller mounted thereon is disclosed. However, the sensor maximum diameter of the rheometer is 60 mm, and even if fibrils are produced by cutting off the outer edge of the obtained disk-like gel, the length of the obtained collagen fibrils is only about 19 cm.

Among conventional orientation techniques other than a shear orientation method, for example, a wet spinning method in which a collagen aqueous solution is discharged into a solvent from a nozzle having a predetermined inner diameter to coagulate collagen is a continuous molding technique in which spinning can continue until a collagen solution in a reservoir is depleted. However, even if collagen discharged from the nozzle into the coagulation liquid is molecularly oriented in the nozzle, since relaxation occurs while the coagulation liquid is gradually replaced with a solvent of the collagen solution, there are problems that almost randomized collagen molecules are converted into fibrils, and collagen fibrils are unlikely to be oriented. In fact, in Non-Patent Document 3, a technique in which, since collagen fibrils within fibers produced by wet spinning are not oriented, fibers are dried while pulling them and thus fibril orientation is caused is disclosed.

In addition, since the wet spinning method is a spinning mechanism in which coagulation gradually occurs from the outside of a linear collagen solution, there is a problem that coagulation is unlikely to occur when the nozzle diameter is larger, and also there is a problem that, for the same reason for controlling the thickness, it is not possible to apply the method for continuous molding of shapes other than a thread shape. For example, when a collagen solution is discharged in a hollow state, the coagulation liquid is unlikely to penetrate into the hollow, and uniform molding becomes difficult. Even if a collagen solution is discharged in a band shape from a slit, it is not possible to maintain the band shape due to slow coagulation, and uniform molding becomes difficult. That is, the wet spinning method has a narrow fibril diameter control range and does not have shape controllability.

Even if other conventional techniques for producing highly oriented collagen fibrils are used, it is not possible to produce collagen fibrils of a certain length or more. In addition to shear stress, a technique for producing collagen fibrils according to an electrochemical method is disclosed (Non-Patent Document 4). This is a technique in which collagen fibers parallel to electrodes are formed at the center of electrodes using a pH gradient occurring between parallel electrodes. However, since it takes 1 hour to precipitate collagen between electrodes, too much time is consumed to perform continuous molding, and in fact, the method described in Non-Patent Document 4 can be called a batch type molding method. Formation of fibers according to this technique is restricted due to the total length of the electrode, and is performed in a batch manner, but it has been recently disclosed that continuous spinning has been developed (Non-Patent Document 5). However, regarding essential problems of the electrochemical method, there are a problem that no apparent fibril orientation occurs and a problem that a collagen fibril diameter converges to about 100 to 150 μm and it is not possible to control the size and shape.

Since a deposition method is a method in which a nozzle and a substrate are caused to move in directions opposite to each other (refer to Patent Document 2), it is not possible to perform continuous spinning. In addition, regarding a magnetic field orientation method, in Patent Document 3, a technique for orienting collagen fibrils without using a superconducting magnet is disclosed. However, this is a batch type production technique that requires 2 hours until collagen is oriented in a Petri dish with a diameter of 20 mm, and it is difficult to apply it to a continuous spinning technique.

The present invention has been made in view of the above circumstances, and an object of the present invention is to provide a highly oriented collagen fibril bundle having a certain fibril length or more which was difficult to produce in the related art.

Solution to Problem

The inventors conducted extensive studies in order to achieve the above object, and as a result, found that it is possible to produce a highly oriented collagen fibril bundle of 1 m or more under predetermined conditions, and completed the present invention.

Specifically, the present invention is as follows.
[1] A uniaxially oriented collagen fibril bundle having a total length in a major axis direction of 1 m or more.
[2] The collagen fibril bundle according to [1], which is highly oriented from the beginning to the end.
[3] A collagen gel containing the collagen fibril bundle according to [1] or [2].
[4] The collagen gel according to [3], which is molded into a string or band shape.
[5] The collagen gel according to [4], wherein the collagen gel has a string form and has a diameter of 0.2 mm or more.
[6] The collagen gel according to any one of [3] to [5], wherein the collagen gel has a cross-sectional area in a range of $3\times10^{-2}$ mm$^2$ to 700 mm$^2$.
[7] The collagen gel according to any one of [3] to [6], wherein a refractive index difference Δn measured according to birefringence measurement at the point of production of the collagen gel is $3\times10^{-4}$ or more.
[8] A dried component of the collagen gel according to any one of [3] to [7].
[9] A method of producing the collagen gel according to any one of [3] to [7], comprising a step of continuously introducing a collagen sol into a flow path maintained at a temperature at which the sol forms gel and orienting collagen fibrils.
[10] The method according to [9], comprising a step of applying shear to a collagen sol containing collagen with a predetermined concentration at a shear rate and for a shear time so that the collagen fibrils are oriented.
[11] The method according to [10], wherein the temperature is in a range of 30° C. to 50° C.
[12] The method according to [10] or [11], wherein the step of applying shear includes a step of increasing the shear stress at a rate of 2% to 40% per second for 2 seconds to 120 seconds due to formation of the collagen fibrils.
[13] The method according to any one of [10] to [12], wherein a collagen concentration of the collagen sol is 1.0 mass % to 10 mass %.
[14] The method according to any one of [10] to [13], wherein the flow path is a cylindrical flow path having a circular or elliptical cross section, and a ratio L/R of a linear velocity L (mm·s$^{-1}$) of a flow rate of the collagen gel to the diameter or minor axis diameter R (mm) of the cross section is in a range of 0.2 to 2 (s$^{-1}$).
[15] The method according to any one of [10] to [13], wherein the flow path is a cylindrical flow path having a rectangular cross section, and a ratio L/X of a linear velocity L (mm·s$^{-1}$) of a flow rate of the collagen gel to a short side X (mm) of the cross section is in a range of 0.2 to 2 (s$^{-1}$).
[16] The method according to any one of [12] to [15], wherein, when the flow path is a cylindrical flow path having a circular or elliptical cross section, the diameter or minor axis diameter of the cross section is R (mm), and when the flow path is a cylindrical flow path having a rectangular cross section, a short side of the cross section is X (mm), and when a time to reach a maximum value or plateau value of the shear stress obtained according to rotation shear stress measurement on the collagen sol using a parallel plate type rheometer in which a sensor gap is set to R/2 (mm) or X/2 (mm), and a sensor temperature is set to an insulation temperature of the flow path is Tau-max(s), the flow path has a flow path length of 20% to 400% of a length calculated by a product of the linear velocity L (mm·s$^{-1}$) of the collagen sol and Tau-max.

Advantageous Effects of Invention

According to the present invention, it is possible to produce a highly oriented collagen fibril bundle having a certain fibril length or more, a collagen gel containing the same, and a molded component thereof.

DESCRIPTION OF EMBODIMENTS

Figure 1:
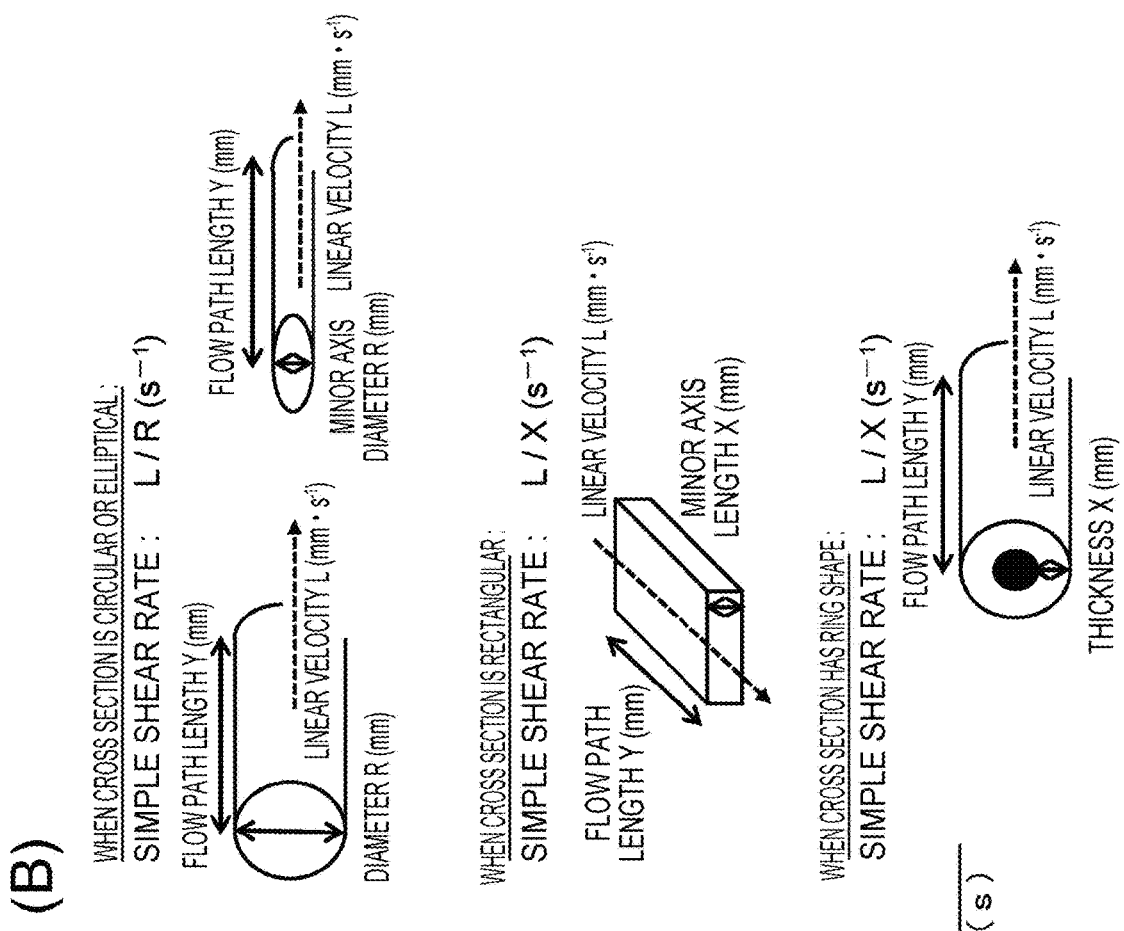
FIG. 1A is a schematic diagram showing a method of measuring a change in shear stress of a collagen sol using a parallel plate type rheometer and deriving a shear stress increase rate and a Tau-max.
FIG. 1B shows a method of calculating a simple shear rate in molds with various shapes.
FIG. 1C shows a method of calculating a flow path length ratio in which a flow path length at which a time for which a collagen sol passes through a flow path is equal to Tau-max is defined as 100%.
Figure 1:
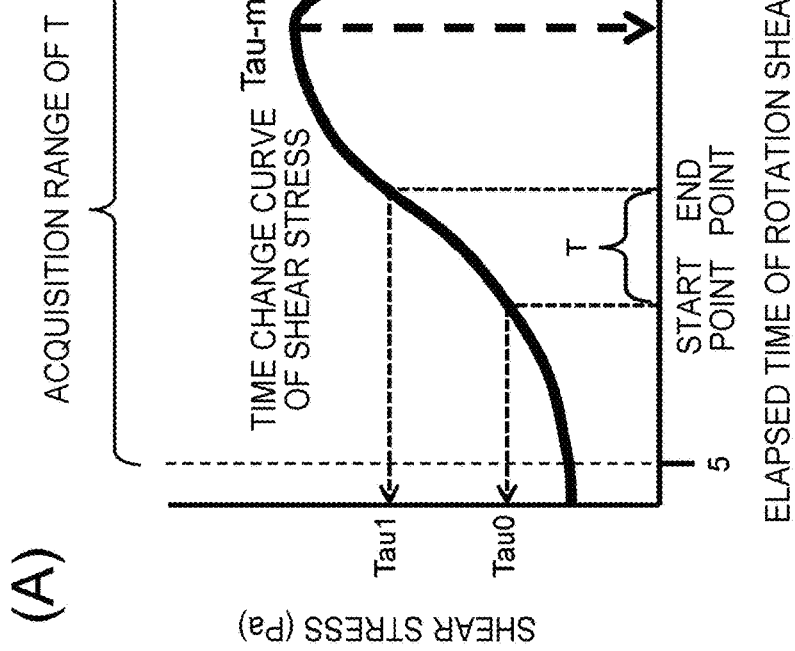

Hereinafter, embodiments (hereinafter simply referred to as the "present embodiment") for realizing the present invention will be described in detail with reference to the drawings as necessary. However, the present invention is not limited to the following present embodiment. The present invention can be variously modified without departing from the sprit and scope of the invention.

A total length of a highly oriented collagen fibril bundle of the present embodiment in the major axis direction is 1 m or more, preferably 2 m or more, and more preferably 10 m or more. The present invention is a modification and development of a batch type collagen fibril orientation method using a rotary rheometer the inventors have found in the past (Patent Document 1) so that the orientation is continuously caused in a mold. In the fibril orientation method of Patent Document 1, a collagen solution with a specific concentration causes rapid fibrillogenesis, and in the procedure, it is required to apply a shear rate significantly lower than in a known shear orientation method by "shear" deformation of a pair of metal plates. In the present invention, in a method that is modified so that a fibril orientation phenomenon similar to that of Patent Document 1 is caused in a flow path into which a collagen solution is introduced, continuous molding is realized through the flow path, and accordingly, for the first time, it is possible to mold a collagen gel of 1 m or more. While not intending to be bound by theory, when collagen fibrils are continuously spun, it is possible to form a fibril bundle with a length of 1 m or more. In principle, there is no limit to the total length of a fibril bundle that can be produced, and it is possible to produce a fibril bundle with a desired length as long as there is a raw material collagen sol. Here, "collagen fibril bundle" used in this specification refers to a bundle of general collagen nanofibrils, and it does not mean that fibrils constituting a bundle each have a length of 1 m or more. In addition, "highly oriented" means a state in which collagen fibrils are highly oriented in a fiber axis direction. For example, high orientation refers to a fibril orientation with a refractive index difference $\Delta n$ of larger than $3 \times 10^{-4}$ measured when a collagen gel is produced and preferably immediately after a collagen gel is produced during measurement of birefringence or a fibril orientation with a birefringence phase difference of 30° to 90° per 1 mm of an optical path length and per 1 mass % of a collagen concentration. The maximum value of the refractive index difference of the collagen gel of the present invention is about $5 \times 10^{-4}$, and when the collagen concentration is 10%, the refractive index difference is about $2 \times 10^{-3}$. However, these values are only examples, and are not intended to limit measurement methods and measurement values, and the orientation of fibrils may be directly observed under an electron microscope. Here, the fibril orientation of collagen can be measured by other methods known to those skilled in the art, but the "high orientation" achieved in the present invention is much higher than the degree of orientation of collagen fibrils produced using a conventional electrochemical method measured using small-angle X-ray scattering or birefringence imaging. In addition, regarding a high orientation range, it is preferable that fibrils be highly oriented from the beginning to the end of fibril bundle and from the surface to the inside of the gel.

The fibril bundle may contain components other than collagen in order to produce a collagen gel or depending on the purpose of the final product, and may contain, for example, a crosslinking agent in order to increase the strength of the collagen gel. In addition, in order to produce artificial bones, collagen fibrils may form a complex with hydroxyapatite (refer to Patent Publication JP-A-2007-98117).

The collagen gel of the present embodiment contains the highly oriented collagen fibrils. Such a collagen gel is produced by a method for producing a collagen gel of the following embodiment. The collagen gel exhibiting the above refractive index difference and birefringence phase difference is regarded as one in which collagen fibrils are sufficiently oriented, for example, are oriented as a fibril bundle with a scale of mm to cm. The refractive index difference when collagen fibrils completely uniaxially oriented are produced does not exceed $10^{-2}$, and its upper limit value is preferably $5 \times 10^{-3}$ or less.

A method of producing a collagen gel containing highly oriented collagen fibrils using shear stress has already been disclosed. The method includes a step in which a collagen sol is continuously introduced into a flow path that is kept at a temperature at which the sol gels so that collagen fibrils are oriented. Methods of orienting collagen fibrils using shear stress are known to those skilled in the art. For example, Patent Document 1 discloses a method of producing a collagen gel comprising a step in which a shear in a shear rate range of $0.20 \ s^{-1}$ to $30 \ s^{-1}$ is applied to a collagen aqueous solution containing collagen with a concentration of 0.50 mass % to 3.0 mass % so that collagen fibrils are oriented, wherein the step includes a step of 2 seconds to 120 seconds in which a shear stress is increased at a rate of 1% to 30% per second due to formation of collagen fibrils so that the collagen fibrils are oriented.

In the present embodiment, the collagen sol is continuously introduced into the flow path while controlling 1) a rate at which fibrillogenesis occurs due to heating when gelling is performed, 2) a shear rate when shear is applied to collagen fibrils, and 3) a shear application time to be within specific ranges. For example, gelling can be performed in a range of 30° C. to 50° C., preferably 35° C. to 45° C. Before the collagen sol is continuously introduced into the flow path, in advance, a rate of the collagen sol is measured in advance using a rotary rheometer. The shear rate at that time is preferably in a range of 2 to 20 $s^{-1}$, for example, 5 $s^{-1}$, in order to promote collagen fibril orientation between flat plates.

As an example of shear conditions for obtaining highly oriented collagen fibrils, a shear application step includes a step of 2 s to 120 s in which a shear stress increases at a rate of 2% to 40% per second due to formation of collagen fibrils. More preferably, a step of 3 s to 60 s in which a shear stress increases at a rate of 4% to 30% per second is included, and more preferable ranges are 5% to 25% and 4 s to 20 s. Thereby, since orientation and gelling of collagen fibrils proceed at the same time, a homogeneous gel molded component having a high collagen fibril orientation is obtained. On the other hand, when rapid fibrillogenesis does not occur in the above step, and collagen fibrillogenesis occurs slowly, shear stress is applied for a long time in a state in which gelling is insufficient, and fibril orientation is disturbed, thereby a molded component with a rough surface being obtained. In addition, also if collagen fibrillogenesis is too fast, a fibrillar network is completed before the orientation proceeds sufficiently, and it is difficult to obtain a gel molded component having a high fibril orientation.

Regarding collagen subjected to gelling, a collagen sol having a collagen concentration of 0.5 mass % to 10 mass % can be used. For example, generally, collagen is commercially available as an acidic aqueous solution having a concentration of about 0.1 to 1%. However, in this specification, collagen which is obtained by concentrating such an aqueous solution and mixing it with a neutral buffer solution, and bringing it into an unstable state (a state in which fibrosis easily occurs) is referred to as a collagen sol. The method of producing a collagen gel of the present embodiment may include a step of preparing such a collagen sol. For example, a collagen sol is prepared by mixing an acidic collagen aqueous solution with a neutral buffer solution, or performing dialysis on a neutral buffer solution.

A collagen sol is a neutral solution containing collagen with a concentration of 0.5 mass % to 10 mass %. Collagen is water-soluble, but a telopeptide-removed collagen which is unlikely to be converted into fibrils near room temperature is preferably contained, and more preferably, it is composed of substantially a telopeptide-removed collagen. The telopeptide-removed collagen is obtained by enzymatically decomposing and removing telopeptides at both ends of collagen molecules using proteolytic enzymes, and for example, obtained by decomposing and removing telopeptides at both ends of collagen molecule by pepsin digestion. In addition, among telopeptide-removed collagens, mammalian-derived telopeptide-removed collagens that have been approved as a medical instrument raw material are preferable, and pig skin-derived telopeptide-removed collagens having excellent thermal stability which have already been clinically applied are more preferably used.

The collagen is not particularly limited as long as it is a collagen having a fiber-forming ability (fiber-forming collagen). Among fiber-forming collagens, type I which is collagen constituting bone, skin, tendons, or ligaments, type II which is a collagen constituting cartilage, type III contained in living tissues composed of type I collagen and the like are preferably used in consideration of ease of availability, abundant research achievements, or similarity to living tissues to which a produced gel is applied. Collagen may be obtained by extraction and purification from living tissues using a general method or commercially available collagen may be used. Collagen may be obtained by purifying each type or a mixture of a plurality of types.

A denaturation temperature of collagen is preferably 32° C. or higher, more preferably 35° C. or higher, and still more preferably 37° C. or higher. When the denaturation temperature is 32° C. or higher, the fluidity of a collagen aqueous solution at room temperature can be maintained for a longer time and denaturation of collagen in a living body is unlikely to occur. The upper limit of the denaturation temperature of collagen is not particularly limited, but it is preferably 50° C. or lower, more preferably 45° C. or lower, and still more preferably 41° C. When the denaturation temperature is 50° C. or lower, collagen fibrosis is accelerated due to the temperature rise, orientation of collagen fibrils is more likely to occur due to shearing, and bioabsorbable properties of collagen are more favorably maintained. The denaturation temperature of collagen is measured by a general method, that is, according to change in circular dichroism, optical rotation, or viscosity according to the temperature rise of the collagen aqueous solution. The denaturation temperature of collagen may be adjusted by selecting collagen having a denaturation temperature within the above numeric range.

In the collagen sol of the present embodiment, the concentration of collagen is 0.5 mass % to 10.0 mass %, preferably 1.0 mass % to 5.0 mass %, and more preferably 2.0 mass % to 3.0 mass % based on the total amount of the collagen sol. When the concentration of collagen is 0.50 mass % or more, breakage of a gel in a collagen gel producing step is reduced, the mechanical strength of the obtained gel can be further improved, and the degree of orientation of collagen fibrils can be increased. On the other hand, when the concentration of collagen is 10 mass % or less, the flowability of the collagen sol at room temperature can be further improved and application of shear becomes easier.

The collagen sol of the present embodiment preferably contains an inorganic salt in order to obtain an ionic strength and pH in suitable ranges to be described below. The inorganic salt is not particularly limited, and examples thereof include sodium chloride, potassium chloride, sodium phosphate, sodium hydrogen phosphate (general term for sodium dihydrogen phosphate and disodium hydrogen phosphate), and potassium hydrogen phosphate (general term for potassium dihydrogen phosphate and dipotassium hydrogen phosphate). Inorganic salts may be used alone or two or more thereof may be used in combination. The collagen sol preferably contains sodium hydrogen phosphate or sodium chloride (salt) among these inorganic salts because in this case the pH of the collagen sol can be easily adjusted to be in a suitable range to be described below and it is harmless to living bodies.

In addition, the collagen sol may contain, as its solvent, a neutral isotonic solution, in order to exhibit two effects: reducing damage to cells and living tissues and causing collagen fibrosis. The neutral isotonic solution may be phosphate buffered saline (PBS) which is used for washing cells and can cause collagen to be actively converted into fibrils.

The ionic strength of the inorganic salt contained in the collagen sol is preferably 0.40 to 1.0, and more preferably 0.60 to 0.80. Here, the ionic strength of the inorganic salt in the present embodiment indicates an ionic strength of all of a plurality of inorganic salts when the collagen sol contains the plurality of inorganic salts. The responsiveness of collagen fibrosis with respect to the temperature is improved as the ionic strength increases. Here, when the ionic strength of the inorganic salt is 0.40 or more, the responsiveness is further improved. In addition, when the ionic strength of the inorganic salt is 1.0 or less, fibrosis at low temperatures is reduced, and the stability of the collagen sol at room temperature is improved (that is, the state of the solution can be maintained for a longer time without fibrosis). Here, in this specification, the ionic strength of the inorganic salt is calculated by adding the product of molar concentrations of respective ions and the square of charge for ionic species derived from all inorganic salts contained in the collagen sol and additionally multiplying it by ½.

The pH (pH at 23° C.; the same in this specification) of the collagen sol of the present embodiment is preferably 6.0 to 9.0, and more preferably 6.5 to 8.0. It is known that collagen fibrosis actively occurs near neutrality. When the pH is 6.0 or more, it is possible to further promote collagen fibrosis. In addition, when the pH is 9.0 or less, it is possible to further promote collagen fibrosis. The pH can be adjusted by a general method, and for example, the pH can be adjusted by controlling the concentration of the inorganic salt contained in the collagen sol, preferably the concentration of sodium chloride and sodium hydrogen phosphate, or adding a strong acid and/or strong alkali such as hydrochloric acid and sodium hydroxide. Here, in this specification, the pH is measured using a pH meter (for example, product name "NAVIh F-71" commercially available from HORIBA, Ltd.).

When the collagen sol contains sodium chloride (salt), the concentration of sodium chloride is not particularly limited as long as the pH and ionic strength of the collagen sol are within desired ranges. For example, the concentration of sodium chloride is preferably 200 mM to 400 mM and more preferably 250 mM to 350 mM with respect to the total amount of the collagen sol. When the concentration of sodium chloride is in such a range, the ionic strength of the inorganic salt is more easily set to be in a range of 0.40 to 1.0 while the pH of the collagen sol is in a range of 6.0 to 9.0.

In addition, when the collagen sol contains sodium hydrogen phosphate, the concentration of sodium hydrogen phosphate is not particularly limited as long as the pH and ionic strength of the collagen sol are within desired ranges. For example, the concentration of sodium hydrogen phosphate is preferably 10 mM to 180 mM and more preferably 20 mM to 140 mM with respect to the total amount of the collagen sol. When the concentration of sodium hydrogen phosphate is in such a range, the ionic strength of the inorganic salt is more easily set to be in a range of 0.40 to 1.0 while the pH of the collagen sol is in a range of 6.0 to 9.0.

A gel of collagen fibrils formed from a collagen sol may have lower strength depending on the collagen concentration and may be damaged during handing such as winding. Here, in order to increase the strength of the collagen gel at an early stage, and collect the collagen gel without damaging, the collagen sol preferably contains a crosslinking agent. When the degree of crosslinking is represented by a consumption rate of amino groups in collagen, it is preferably in a range of 5% to 80%. The crosslinking agent is not particularly limited. Crosslinking agents can be used alone or two or more thereof can be used in combination. Plant-derived genipin, which is considered as a crosslinking agent having low cytotoxicity, 1-(3-dimethylaminopropyl)-3-ethylcarbodiimide (hereinafter referred to as "EDC") which is removed by washing because a crosslinking agent is not inserted between collagen molecules, its crosslinking aid N-hydroxysuccinimide (NHS), or the like is preferably used. Genipin is an aglycone of geniposide, and is obtained by, for example, oxidation, reduction, and hydrolysis of geniposide, or enzymatic hydrolysis of geniposide. Geniposide is an iridoid glycoside contained in *gardenia* of the family Rubiaceae, and is obtained by extraction from *gardenia*. Genipin is represented by a molecular formula of $C_{11}H_{14}O_5$, and may be synthesized by a general method or is commercially available. In addition, genipin may be converted into derivatives to the extent that achievement of objects of the present invention is not impaired and the crosslinking effect thereof is secured. EDC is a kind of water soluble carbodiimide, and any kind of water soluble carbodiimide can be used as a crosslinking agent. Among water soluble carbodiimides, inexpensive and highly safe EDC is particularly preferably used. Water soluble carbodiimides may be alone or two or more thereof may be used in combination. In addition, EDC may be used alone or a mixture with NHS may be used. It is known that the crosslinking activity of EDC is improved when mixed with NHS.

When the collagen sol of the present embodiment contains a crosslinking agent, and the crosslinking agent is genipin, the concentration of genipin is preferably 0.5 mM to 5.0 mM, more preferably 1.0 mM to 4.0 mM, and still more preferably 2.0 mM to 3.0 mM with respect to the total amount of the collagen sol. When the concentration of genipin is 0.5 mM or more, the strength of the collagen gel can increase at an early stage, and the collagen gel is unlikely to be broken when it is collected, and thus the yield is improved. On the other hand, when the concentration of genipin is 5.0 mM or less, the flowability of the collagen sol at room temperature can be maintained more favorably, and cytotoxic effects of genipin can be reduced.

When the collagen sol of the present embodiment contains a crosslinking agent, and the crosslinking agent is EDC, the concentration of EDC is preferably 1.0 mM to 20 mM, more preferably 2.0 mM to 10 mM, and still more preferably 3.0 mM to 8.0 mM with respect to the total amount of the collagen sol. The effect obtained when the concentration of EDC is in a range of 1.0 mM to 20 mM is similar to that of genipin. It is preferable to mix NHS with EDC because the crosslinking activity increases. A molar ratio (EDC:NHS) between EDC and NHS is preferably in a range of 10:1 to 1:1. In such a range, the crosslinking activity of EDC can increase, and cytotoxic effects resulting from the remaining NHS can be further reduced.

In addition, the collagen sol of the present embodiment may further contain various solvents and additives used in conventional collagen sols. Examples of such solvents and additives include acids such as dilute hydrochloric acid, citric acid, and acetic acid, and buffer agents such as N-2-hydroxyethylpiperazine-N'-2-ethanesulfonic acid (HEPES) and trishydroxymethylaminomethane (Tris).

The above additives and solvents may be used alone or two or more thereof may be used in combination. In addition, the contents of the additive and solvent in the collagen sol are not particularly limited as long as achievement of objects of the present invention is not impaired.

The method of producing a collagen gel of the present embodiment includes a step of increasing shear stress generated when shear is applied to a collagen sol due to formation of collagen fibrils (hereinafter referred to as a "fiber forming step"). Since it is not possible to directly measure the shear stress in the flow path, it is possible to estimate a "shear stress increase rate" according to rotation measurement using a rheometer described in Patent Document 1 using the half value (R/2) of the diameter or the minor axis diameter R (mm) as a sensor gap when the cross section of the flow path is circular or elliptical, and using the half value (X/2) of the short side X (mm) of the rectangular cross section as a sensor gap when the cross section of the flow path is rectangular. It is desirable that the shear rate in rotation measurement be the same as the actual shear rate in the flow path, but a difference within one digit is acceptable. The set temperature of the rheometer is set to be the same as a collagen gel production temperature. In at least a part of the fiber forming step, a shear rate in a specific range (the range will be described below) is applied to the collagen sol. In addition, during application of shear at such a shear rate, a step in which a rate (ratio) of increasing shear stress of the collagen sol is in a range of 2% to 40% per second is performed for 2 seconds to 120 seconds. Here, an increase rate of shear stress per second (hereinafter referred to as a "shear stress increase rate") is calculated by the following Formula (1).

$$\text{Shear stress increase rate (\%)} = (Tau1 - Tau0)/Tau0/T \times 100 \quad (1)$$

In Formula (1), Tau0 indicates the shear stress at the start point of a period for which a shear stress increase rate is calculated, and Tau1 indicates the shear stress at the end point of the period for which a shear stress increase rate is calculated. "T" indicates a length (unit: seconds) of the period for which a shear stress increase rate is calculated, and is calculated in an arbitrary range of $5.0 \leq T \leq 120$. Even if the increase in shear stress is instantaneously high only at a certain time, since it is not sufficient for orientation of collagen, a shear stress increase rate is calculated in a period of 5.0 seconds or longer. On the other hand, since shear is applied for a period of 120 seconds or shorter, a period for which a shear stress increase rate is calculated is also 120 seconds or shorter. The shear stress increase rate estimated in this manner is an estimate of increase in shear stress generated in the flow path and is also an indicator of a rate of fibrosis. A higher shear stress increase rate indicates a faster rate of fibrosis.

In the fiber forming step according to the present embodiment, formation of collagen fibrils is performed by, for example, warming of the collagen sol. When the pH of the collagen sol containing an inorganic salt is 6.0 to 9.0, and the ionic strength is 0.40 to 1.0, collagen molecules are self-assembled according to hydrophobic and electrostatic interactions due to warming and form fibrils. When a collagen sol is heated, it is preferable to form collagen fibrils by warming the sol at a temperature from 25° C. or lower to 30° C. to 50° C. When the collagen sol is warmed at a temperature from 25° C. or lower, it is possible to further reduce formation of collagen fibrils before warming starts. On the other hand, when the collagen sol is warmed to a temperature of 30° C. or higher, a rate of formation of collagen fibrils can be higher, and when the collagen sol is warmed to a temperature of 50° C. or lower, it is possible to prevent thermal denaturation of collagen more effectively and reliably. Here, when collagen fibrils are formed by warming, the increase in shear stress may start later than the increase in temperature, and after a desired warming temperature (for example, 30° C. to 50° C.) is reached, the shear stress may increase while the temperature is maintained.

In the method of producing a collagen gel of the present embodiment, conditions (a concentration and composition of a collagen sol, a flow rate, a flow path shape, and a flow path temperature) are set so that the shear stress increase rate of the collagen sol in the flow path is in a range of 2% or more and 40% or less, and collagen fibrils are oriented. When a shear stress increase rate in a range of 2% or more is caused in the flow path, it is possible to arrange collagen fibrils in the uniaxial direction and continuously mold the collagen gel, and it is possible to continuously mold a gel having further improved orientation of collagen fibrils. On the other hand, when shear is applied at a shear stress increase rate in a range of 40% or less, it is possible to prevent the collagen gel from being fixed before sufficient collagen fibrils are arranged in the uniaxial direction. For example, even if a collagen sol is introduced into a heated flow path to increase the shear stress, it is caused to pass through the flow path at a shear stress increase rate in a range of 40% or less, and thus a difference in the degree of fibrosis between the outside and the inside of the flow path is unlikely to occur.

The flow path through which a collagen sol flows may be a cylindrical flow path having a circular or elliptical cross section, and may have a rectangular cross section, or a ring-shaped cross section in which a cylinder or elliptical cylinder is positioned at the center of a cylindrical flow path having a circular or elliptical cross section. Materials of components constituting the flow path are not particularly limited, and for example, materials having high thermal conductivity, for example, metals such as stainless steel, copper, and aluminum, are preferable. In order to reduce frictional resistance and corrosion of the surface, the surface of a metal may be covered with a polymer such as polytetrafluoroethylene. A polymer material having low thermal conductivity can also be used by applying a method of reducing the thickness and promoting thermal conduction.

When a collagen sol is introduced into the above flow path, a specific shear rate is applied to the collagen sol. A method of calculating a shear rate in the flow path and an appropriate shear rate in the present invention will be described below:

(1) Flow Path Having a Circular or Elliptical Cross Section

When the diameter or minor axis diameter of the cross section is R (mm), a ratio L/R of the flow rate of the collagen gel represented by the linear velocity L (mm·s$^{-1}$) to R is a shear rate, and it is adjusted to be in a range of 0.2 to 2 (s$^{-1}$). The linear velocity L is calculated by dividing the flow rate (mm$^3$·s$^{-1}$) of the collagen sol introduced into the flow path by a cross-sectional area of the flow path. Thereby, it is possible to continuously mold a homogeneous gel molded component having a high collagen fibril orientation. When L/R is less than 0.2 (s$^{-1}$), the shear rate in the flow path is too low, and it is difficult to sufficiently improve the orientation of collagen fibrils. On the other hand, when L/R exceeds 2 (s$^{-1}$), the orientation of collagen fibrils is too high, but a frictional force is too high and a molded component with a rough surface or a molded component having an uneven internal structure is likely to be formed.

(2) Flow Path Having a Rectangular Cross Section

When the short side of the rectangular cross section is X (mm), a ratio L/X of the flow rate of the collagen gel represented by the linear velocity L (mm·s$^{-1}$) to X is a shear rate, and it is adjusted to be within a range of 0.2 to 2 (s$^{-1}$). A method of calculating a linear velocity and the effect when the shear rate is outside the range are the same as in the above (1).

(3) Flow Path Having a Ring-Shaped Cross Section

Calculation is performed in the same manner as in the above (2), where the cross section of the ring is X, and L/X is a shear rate, and is adjusted to be within a range of 0.2 to 2 (s$^{-1}$). A method of calculating a linear velocity and the effect when the shear rate is outside the range are the same as in the above (1).

The length of the flow path is adjusted to be within an appropriate range. When a time to reach a maximum value or plateau value of the obtained shear stress is Tau-max(s) according to rotation measurement using a rheometer for calculating a stress increase rate, the length of the flow path is adjusted so that the flow path has a flow path length of 20% to 400% of the length calculated by a product of the linear velocity L (mm·s$^{-1}$) of the collagen sol and Tau-max. Thereby, fibrosis rapidly occurs, and as a result, a homogeneous gel molded component having a high collagen fibril orientation is obtained. On the other hand, when the flow path length is less than 20%, since release occurs due to shear stress before sufficient orientation proceeds, the fibril orientation in the molded component tends to decrease. In addition, when the flow path length exceeds 400%, since friction and shear are continuously applied even if the fibril orientation and gelling are completed, a molded component with a rough surface or a molded component having an uneven internal structure tends to be formed.

A device for introducing a collagen sol into a flow path is not particularly limited as long as it can adjust the flow rate constantly. A pump of a type in which a feed screw is rotated by a motor for driving (general name: syringe pump) is preferably used in consideration of high torque and accuracy.

Regarding a method of heating a flow path, a method in which a mold constituting a flow path is immersed in a water bath at a desired temperature, a method of arranging a flow path in a warmer, a method of circulating a liquid at a desired temperature around a mold, and a method of covering a mold with a heater can be used. Among these methods, in consideration of temperature controllability and simplicity, a method of immersing in a water bath and a method of covering a mold with a heater are preferably used.

The collagen gel of the present embodiment contains a highly oriented collagen fibril bundle. The shape of the collagen gel is not particularly limited, and can be molded into a desired shape according to the purpose, but is preferably molded into a string or band shape. The shape and size of the collagen gel can be appropriately changed according to the shape and size of the flow path or a mold connected to an outlet thereof. When the form is a string shape, the diameter of the string-like collagen gel may be 0.2 mm or more. In addition, the cross-sectional area may be in a range of $3 \times 10^{-2}$ mm$^2$ to 700 mm$^2$. In the case of medical collagen, for example, the collagen gel is intended to have a diameter that is adjusted to be within a range of 1 to 10 mm. In addition, a plurality of collagen gels may be produced at the same time by connecting a plurality of flow paths in a direction perpendicular to the flow direction, and a desired waveform may be applied to a collagen gel by moving a flow path.

The collagen gel of the present embodiment is highly oriented, and its refractive index difference Δn may be $3 \times 10^{-4}$ or more. The refractive index difference is calculated by dividing a retardation (nm) measured using a known 2D birefringence measurement device by the thickness of a specimen, that is, a distance that light has passed. For the retardation (nm) in this case, an average value of line analysis (n=5) is used so that values of local parts having a particularly high orientation are not used. In measurement of birefringence for calculating a refractive index difference Δn used in the present invention, the collagen gel that contains water is measured immediately after production. The thickness of the gel can be adjusted and determined by inserting a spacer of which the thickness is known between two slide glasses.

In addition, the obtained collagen gel can be appropriately dried depending on the purpose, and a collagen fibril bundle as a dried component can be provided. A method of drying a collagen gel can be a method known to those skilled in the art such as freeze-drying.

Applications of the collagen fibril bundle of the present embodiment or the gel containing the same are not particularly limited, and an implant for a living body, and particularly, collagen fibrils oriented as a fibril bundle with a scale of mm to cm can be obtained, and it is expected to be beneficial as an artificial tendon according to the size. In addition, the present embodiment is also beneficial in that such oriented collagen fibrils can be formed non-destructively and efficiently (for example, within 20 minutes). Here, when the collagen gel of the present embodiment is used as an implant for a living body such as an artificial tendon, a plurality of collagen gels obtained by a plurality of production methods may be laminated or composited as necessary. In addition, a plurality of collagen gels may be twisted to form a composite.

EXAMPLES

While the present invention will be described below in more detail with reference to examples, the present invention is not limited to these examples.

Example 1

Neutral Phosphate Buffer Solution Containing Sodium Chloride

A 50 mM disodium hydrogen phosphate aqueous solution containing 140 mM sodium chloride and a 50 mM sodium dihydrogen phosphate aqueous solution containing the same concentration of sodium chloride were mixed to prepare a buffer solution (1×NPB) with a pH of 7. In the same step, n×NPB (n is an integer) was prepared.

Collagen Sol

An acidic collagen aqueous solution with a concentration of 1.0% (derived from pig skin; commercially available from NH Foods Ltd.) was concentrated using a rotary evaporator at 29° C. to prepare a collagen aqueous solution with a concentration of 3.0%. 5 mL of 12×NPB was added to 25 g of the collagen aqueous solution with a concentration of 3.0% put into a centrifuge tube with a capacity of 50 mL, and a stirrer was accommodated and shaken to prepare a collagen sol A with a concentration of 2.5% using 2×NPB as a solvent. Bubbles contained in the collagen sol were removed using a centrifuge (10° C., 10,000×g, 40 minutes). The shear stress of the collagen sol A obtained using a parallel plate type rheometer (HAAKE Mars III commercially available from Thermo Fisher Scientific K.K.) is shown in the following Table 1. The method described in Patent Document 1 (FIG. 1) was directly used to calculate a Tau increase rate, and Tau-max was calculated as above.

Collagen sols B and C with a concentration of 2.5% were prepared in the same method as in the collagen sol A except that 1.5×NPB and 1×NPB were used as solvents. The obtained shear stresses are shown in the following Table 1.

TABLE 1

Table 1 Change in shear stress of three types of collagen sols measured using parallel plate type rheometer

| Collagen sol | | Rheometer measurement conditions | | Start point | | End point | | Increase period | Shear stress increase | Tau-max |
|---|---|---|---|---|---|---|---|---|---|---|
| | Concentration (wt %) | NPB factor | Shear rate ($S^{-1}$) | Gap (mm) | $T_0$ (s) | $Tau_0$ (Pa) | $T_1$ (s) | $Tau_1$ (Pa) | T (s) | rate (% · $s^{-1}$) | (s) |
| A | 2.5 | 2 | 5 | 1.42 | 18 | 95 | 26 | 126 | 8 | 4.1 | 28 |
| A | 2.5 | 2 | 5 | 1 | 9 | 81 | 18 | 138 | 9 | 7.8 | 21 |
| A | 2.5 | 2 | 5 | 0.45 | 9 | 93 | 15 | 215 | 6 | 22 | 15 |
| B | 2.5 | 1.5 | 5 | 1 | 38 | 57 | 50 | 69 | 12 | 1.7 | 60 |
| C | 2.5 | 1 | 5 | 1 | 70 | 48 | 94 | 50 | 24 | 0.17 | 132 |

Spinning

Figure 2:
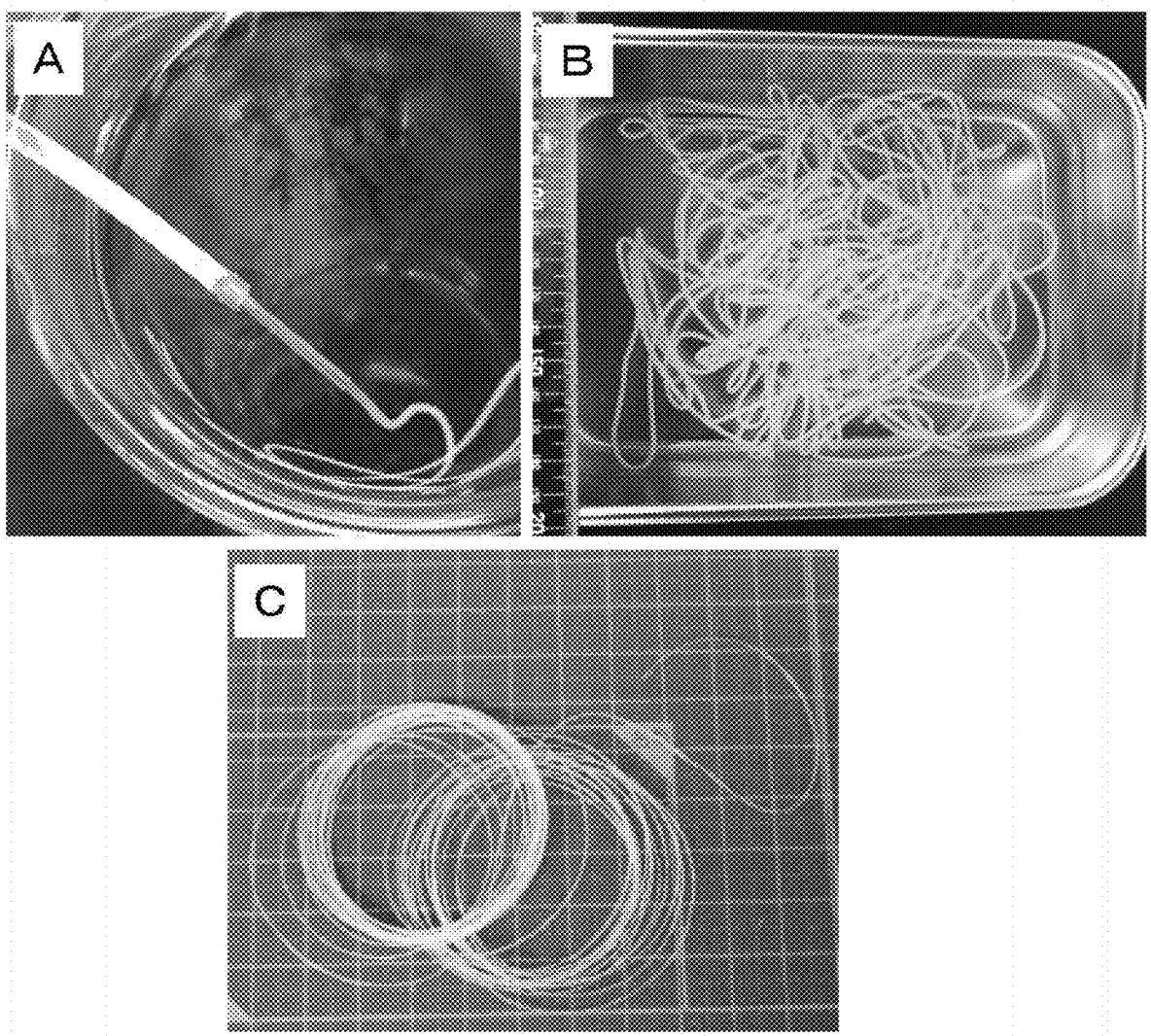
FIG. 2A shows a state of spinning in Example 1.
FIG. 2B shows the appearance of a string-like collagen gel obtained in Example 1.
FIG. 2C shows the appearance of dry fibers produced from the string-like collagen gel in obtained Example 2.

The collagen sol was accommodated in a syringe with a capacity of 30 mL (commercially available from Terumo Corporation), which was connected to a stainless steel tube (with an inner diameter of 2.00 mm×26.3 mm) via a silicone rubber tube with a length of 25 cm. Only the stainless steel tube was immersed in 2×NPB in a 1 L beaker warmed to a range of 37.5° C. to 38.1° C. in a water bath, and the collagen sol was sent from the syringe to the stainless steel tube at a constant rate (14.1 mL·$h^{-1}$) using a syringe pump. Details of production conditions designed based on the calculation method shown in FIGS. 1B and 1C such as a simple shear rate represented by a ratio L/R of a flow rate L (mm·$s^{-1}$) of collagen to a diameter R (m) of a cross section of a flow path and a flow path length ratio derived from the relationship of collagen sol used and Tau-max are shown in the following Table 2. A polyethylene bag containing crushed ice was placed on the syringe, and heating of the collagen sol was restricted. A cloudy string-like collagen gel was continuously discharged from the tip of the stainless steel tube until the collagen sol in the syringe disappeared, and gel fibrils were precipitated on the bottom of the beaker (FIG. 2A).

TABLE 2

Condition for producing oriented collagen fibrillar gel molded component

| | Sol | | | | Flow path | | | | Shear rate | Flow path length | |
|---|---|---|---|---|---|---|---|---|---|---|---|
| | Type | Tau increase rate (s) | Tau-max (s) | Flow rate L (mm · $s^{-1}$) | Cross section Shape | Diameter R (mm) | Short side X (mm) | Length Y (mm) | L/R or X/R ($s^{-1}$) | ration calculation L × Tau-max (mm) | Flow path length ratio 100Y/ (L × Tau-max) (%) |
| Example 1 | A | 7.8 | 21 | 1.25 | Circular | 2.00 | — | 26.3 | 0.62 | 26 | 100 |
| Example 2 | A | 7.8 | 21 | 2.50 | Circular | 2.00 | — | 52.5 | 1.3 | 53 | 100 |
| Example 3 | A | 7.8 | 21 | 1.25 | Circular | 2.00 | — | 52.5 | 0.62 | 26 | 200 |
| Example 4 | A | 7.8 | 21 | 1.25 | Circular | 2.00 | — | 78.8 | 0.62 | 26 | 300 |
| Example 5 | A | 4.1 | 28 | 3.55 | Circular | 2.84 | — | 99.4 | 1.3 | 99 | 100 |
| Example 6 | A | 22 | 15 | 1.13 | Circular | 0.90 | — | 16.9 | 1.3 | 17 | 100 |
| Example 7 | A | 7.8 | 21 | 2.38 | Rectangular | — | 1.00 | 50 | 1.2 | 38 | 130 |
| Comparative Example 1 | A | 7.8 | 21 | 5.00 | Circular | 2.00 | — | 105 | 2.5 | 105 | 100 |
| Comparative Example 2 | A | 7.8 | 21 | 1.25 | Circular | 2.00 | — | 5 | 0.62 | 26 | 19 |
| Comparative Example 3 | A | 7.8 | 21 | 0.47 | Circular | 2.00 | — | 26.3 | 0.13 | 9.5 | 270 |
| Comparative Example 5 | B | 1.7 | 60 | 1.25 | Circular | 2.00 | — | 75 | 0.62 | 75 | 100 |
| Comparative Example 6 | C | 0.17 | 132 | 1.25 | Circular | 2.00 | — | 75 | 0.62 | 165 | 46 |

After spinning was completed, the excess 2×NPB was removed, and 1-ethyl-3-(3-dimethylaminopropyl)carbodiimide hydrochloride (EDC) powder and N-hydroxysuccinimide (NHS) were added to the collagen gel so that their concentrations became 50 mM and 10 mM, respectively, and the mixture was left in an incubator at 37° C. for 12 hours to introduce crosslinks into collagen. Then, 2×NPB was discarded, washing with deionized water was repeated, and the resultant was stored in 20% ethanol (FIG. 2B).

Figure 3:
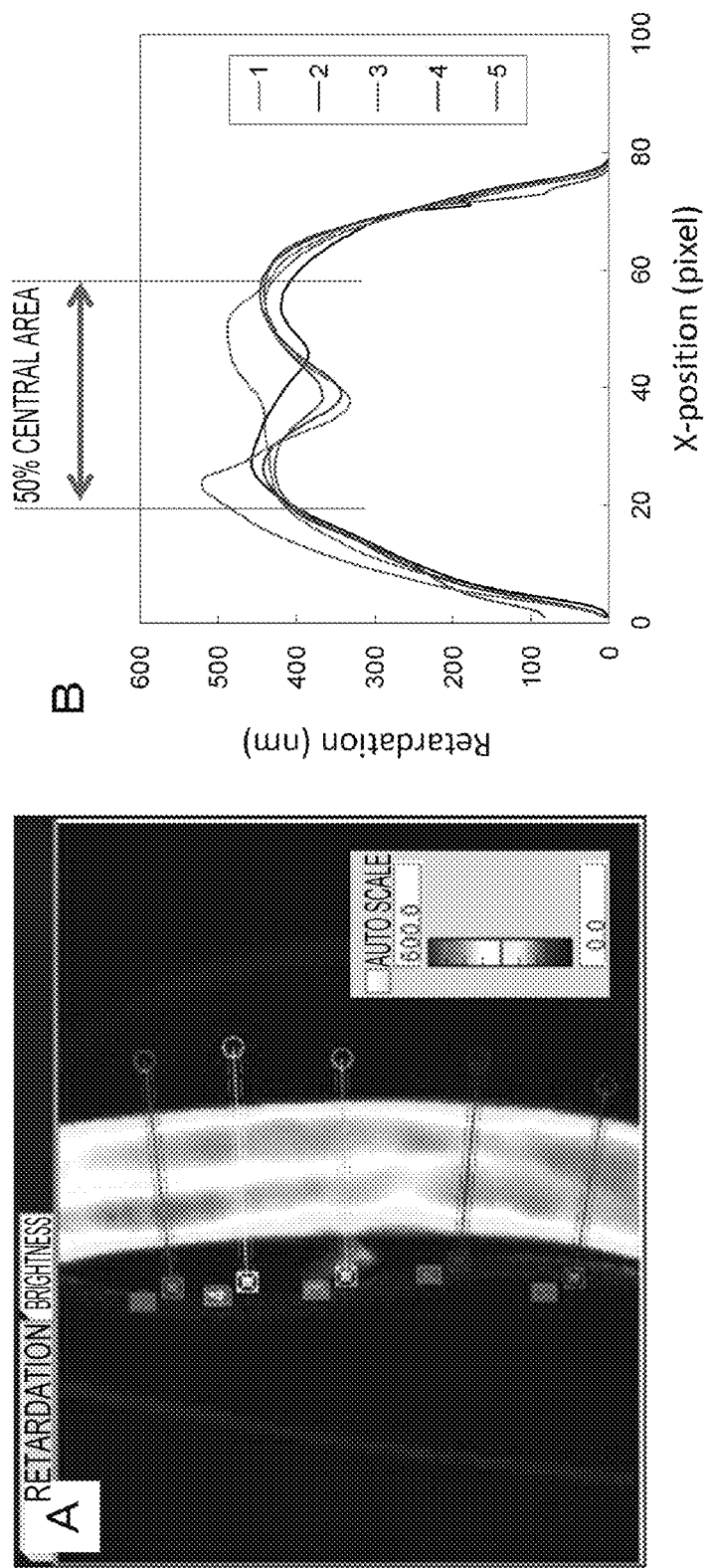
FIG. 3A shows a 2D birefringence image of the string-like collagen gel in Example 1 and FIG. 3B shows line analysis data. Line analysis was performed at an arbitrary five points perpendicular to the axial direction of the string. Regarding retardation, an average value of the 50% central area was used.

Evaluation of Collagen Fibril Orientation Using 2D Birefringence Measurement Device The obtained string-like collagen gel was returned to deionized water, and then a silicone rubber with a thickness of 1 mm was inserted as a spacer between two slide glasses. A 2D birefringence image was obtained using a 2D birefringence measurement device (FIG. 3A). Line analysis was performed at five points on the image, an average value of the 50% central area in the width of the specimen was obtained as shown in FIG. 3B, and the retardation (nm) of collagen fibers was obtained. Δn was calculated by dividing the retardation by a thickness of 1 mm.

Evaluation of Collagen Fibril Orientation Under Scanning Electron Microscope (SEM)

The string-like collagen gel was fixed with glutaraldehyde, and t-butanol freeze-dry was then performed according to a general method, and thereby a dried sample was obtained. The sample was torn in the axial direction of the string, the exposed cross section was coated with gold, and SEM observation was performed using JSM-6490LA (commercially available from JEOL Ltd.).

Evaluation

Figure 4:
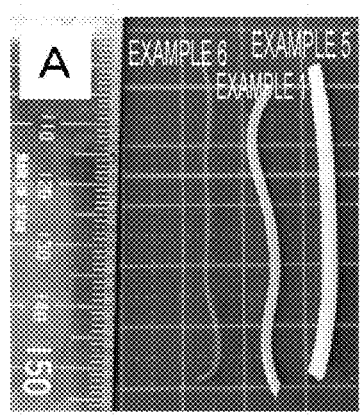
FIG. 4A shows the appearance of string-like collagen gels produced using stainless steel tubes with different inner diameters and FIG. 4B shows the relationship between a cross-sectional area of the gel and a cross-sectional area of the obtained dry fibers.
Figure 4:
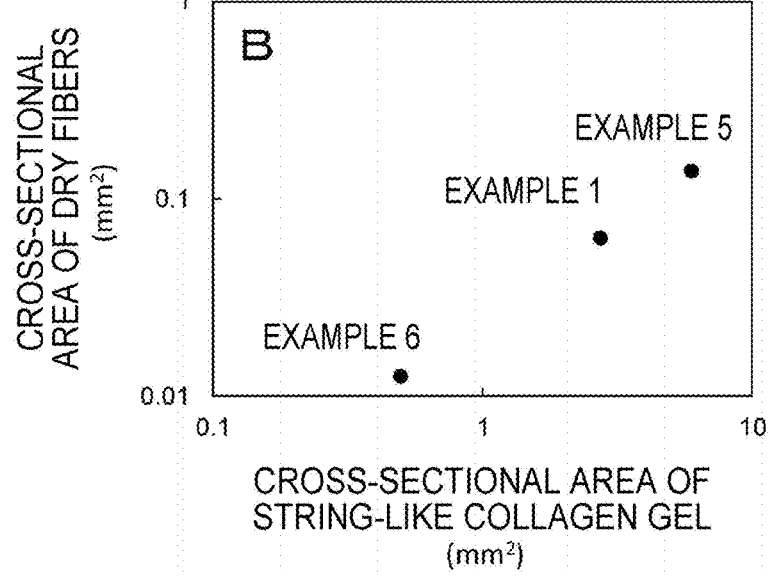
Figure 5:
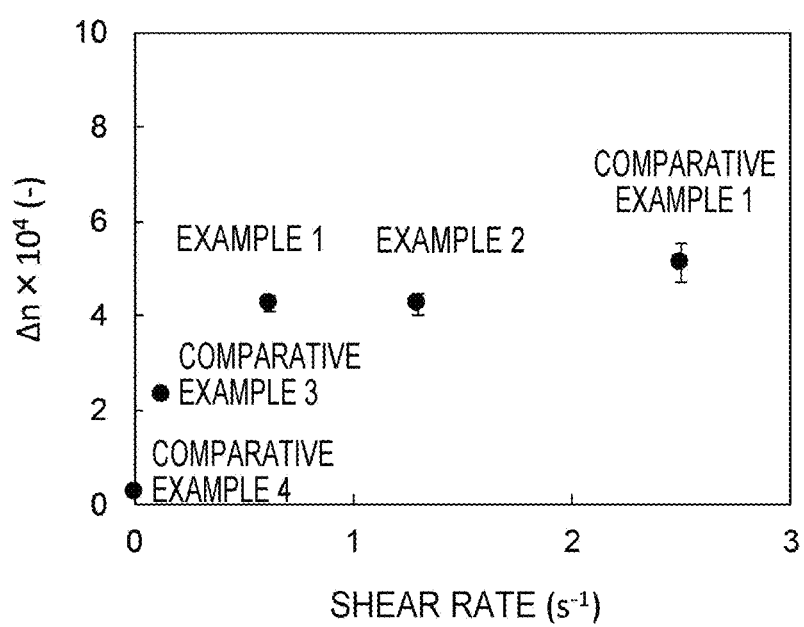
FIG. 5 is a diagram showing the relationship between a shear rate of the collagen sol in the stainless steel tube and a refractive index difference $\Delta n$ of the obtained collagen gel.
Figure 6:
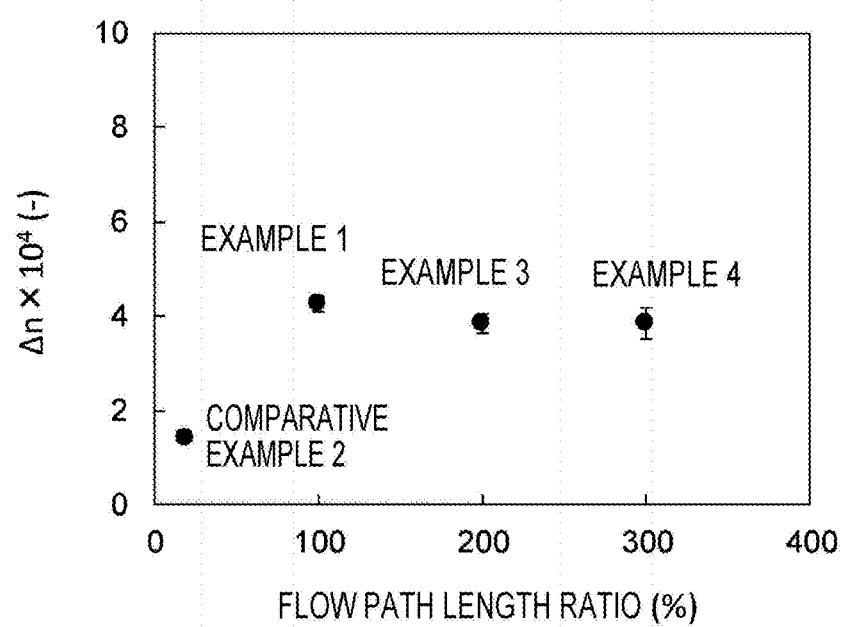
FIG. 6 is a diagram showing the relationship between a flow path length ratio of a stainless steel tube with respect to ideal conditions and a refractive index difference $\Delta n$ of the obtained collagen gel.
Figure 7:
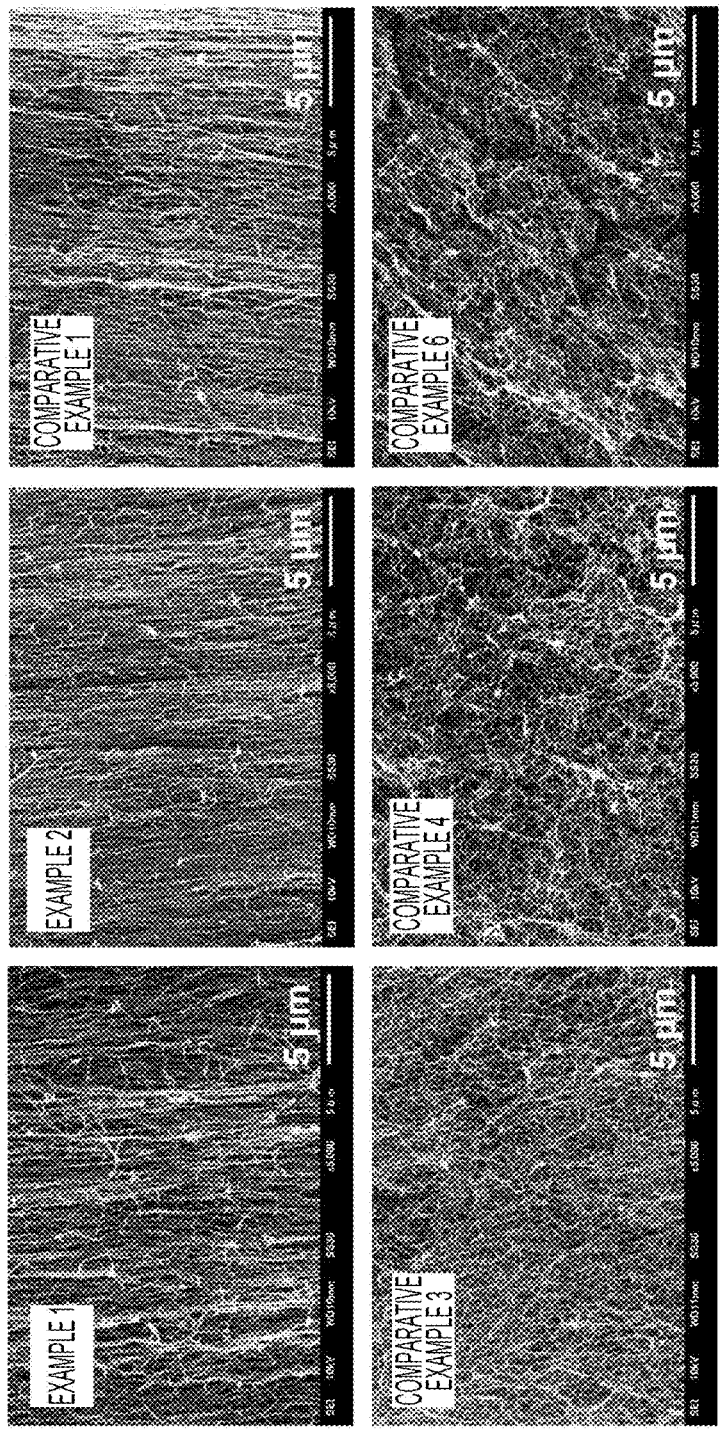
FIG. 7 shows images of the inside of string-like collagen gels under a scanning electron microscope (SEM).

The obtained collagen gel had a diameter that was substantially equal to the inner diameter of the flow path (FIG. 4A) and had a cross-sectional area of 2.78±0.06 mm² (FIG. 4B), had a refractive index difference of $4.25 \times 10^{-4}$, and exhibited high collagen fibril orientation (FIG. 5 and FIG. 6). The orientation of collagen fibrils was confirmed in SEM observation (FIG. 7). Thick dried collagen fibers having a cross-sectional area of $6.21 \times 10^{-2} \pm 0.40 \times 10^{-2}$ mm² were obtained from such a thick string-like collagen gel (FIG. 4B). The total length of the dried collagen fiber was 9 m, and the total length of gel fibrils was estimated to be 9 m.

Example 2

A string-like collagen fibrillar gel was produced and evaluated in the same manner as in Example 1 except that production conditions were changed as shown in Table 2. In addition, in Example 2, the following sample was prepared from the string-like collagen fibrillar gel, and a tensile test was performed.

Production of Dried Collagen Fibers

EDC/NHS crosslinked collagen gel fibrils stored in 20% ethanol were gradually moved to 50% ethanol and 90% ethanol, and wound on a foamed polyethylene rod (with a diameter of 42 mm), and air-drying was performed at room temperature. Since no apparent contraction of collagen fibers in the axial direction occurred before and after drying, the length of gel fibrils was estimated by measuring the total length. The obtained collagen fibers were vacuum-dried at 130° C. for 12 hours, and dehydrated thermal crosslinks were introduced (referred to as dry fibers). The dry fibers were cut with a razor blade, cross section images were obtained using a Table Top SEM (Miniscope TM3000, commercially available from Hitachi High-Technologies Corporation), and cross-sectional areas (average value, n=5) were measured using image analysis software ImageJ.

Production of Wet Collagen Fibers

Some of the dry fibers were immersed in PBS at room temperature for 6 hours to absorb water, and thereby wet collagen fibers were obtained (referred to as wet fibers). The wet fibers were cut with a razor blade, cross section images were obtained using an upright microscope (BX53, commercially available from Olympus Corporation), and cross-sectional areas (average value, n=5) were measured using image analysis software ImageJ.

A tensile test was performed on the dry fibers and the wet fibers using a texture analyzer TA. XT. Plus (commercially available from Stable Micro Systems). The fibers were cut at intervals of about 25 cm, wound around a tension jig A/SPR (composed of a pair of parallel cylinders), and a tensile test in which a distance between parallel cylinders increased at a rate of 2 mm/sec was performed until breaking occurred. Using the fibercross-sectional area and the initial fibril length, the obtained load-displacement curve was converted into a stress-strain curve, and a Young's modulus was obtained from the initial straight line area, and breaking stress and breaking strain were obtained from the breaking point.

Evaluation

When the collagen sol A that was rapidly converted into fibrils was supplied to a flow path with a predetermined length at a predetermined shear rate as shown in Table 2, a thick string-like collagen gel that has been completely gelled and having the same size as the stainless steel tube was discharged from the outlet of the flow path as in Example 1. The obtained collagen gel had a refractive index difference of $4.25 \times 10^{-4}$ and exhibited a high collagen fibril orientation (FIG. 5). Since the orientation of collagen fibrils inside was high, a Young's modulus and breaking stress were significantly high in the fiber axis direction both in the dry state and the wet state simulating an actual operation environment compared to Comparative Example 2 produced under conditions in which the degree of orientation decreased and using a stainless steel tube having the same inner diameter (FIGS. 8A, 8B, 8D, and 8E). The breaking strain was significantly larger in the dry state than in Comparative Example 2 (FIG. 8C), and did not exhibit a statistically significant difference in the wet state but tended to be high (FIG. 8F). The total length of the dried collagen fiber was 9 m, and the total length of gel fibrils was estimated to be 9 m.

Example 3

A string-like collagen fibrillar gel was produced and evaluated in the same manner as in Example 1 except that production conditions were changed as shown in Table 2.

Evaluation

When the collagen sol A that was rapidly converted into fibrils was supplied to a flow path with a predetermined length at a predetermined shear rate as shown in Table 2, a thick string-like collagen gel that has been completely gelled and having the same size as the stainless steel tube was discharged from the outlet of the flow path as in Example 1. The obtained collagen gel had a refractive index difference of $3.83 \times 10^{-4}$ and exhibited a high collagen fibril orientation (FIG. 6). The total length of dried collagen fibers was 9 m, and the total length of gel fibrils was estimated to be 9 m.

Example 4

A string-like collagen fibrillar gel was produced and evaluated in the same manner as in Example 1 except that production conditions were changed as shown in Table 2.

Evaluation

When the collagen sol A that was rapidly converted into fibrils was supplied to a flow path with a predetermined length at a predetermined shear rate as shown in Table 2, a thick string-like collagen gel that has been completely gelled and having the same size as the stainless steel tube was discharged from the outlet of the flow path as in Example 1. The obtained collagen gel had a refractive index difference of $3.82 \times 10^{-4}$ and exhibited a high collagen fibril orientation (FIG. 6). The total length of the dried collagen fibril was 9 m, and the total length of gel fibrils was estimated to be 9 m.

Example 5

A string-like collagen fibrillar gel was produced and evaluated in the same manner as in Example 1 except that production conditions were changed as shown in Table 2. Dry fibers and wet fibers were produced in the same manner as in Example 2, and a tensile test was performed.

Evaluation

Figure 8:
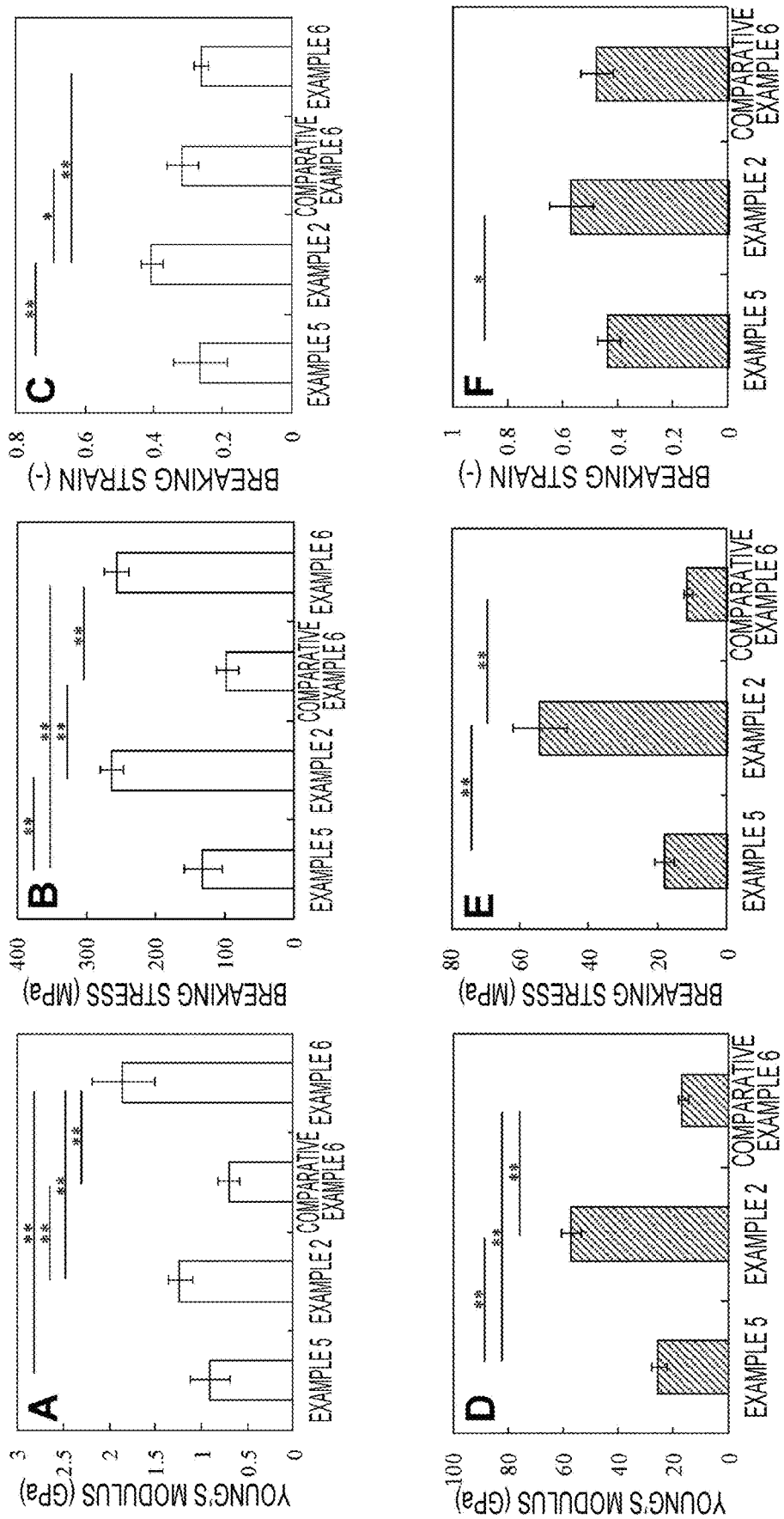
FIG. 8A shows the Young's modulus of collagen fibers (dry fibers) obtained by drying the string-like collagen gels.
FIG. 8B shows the breaking stress.
FIG. 8C shows the breaking strain.
FIG. 8D shows the Young's modulus of wet collagen fibers (wet fibers) in which dry fibers are immersed in a phosphate buffer solution.
FIG. 8E shows the breaking stress.
FIG. 8F shows the breaking strain. Data is shown as average value±standard deviation (n=5). The difference between data groups was measured according to the Tukey's test, and p<0.05 (* in the drawing) was defined as a significant difference. ** indicates p<0.01.
Figure 9:
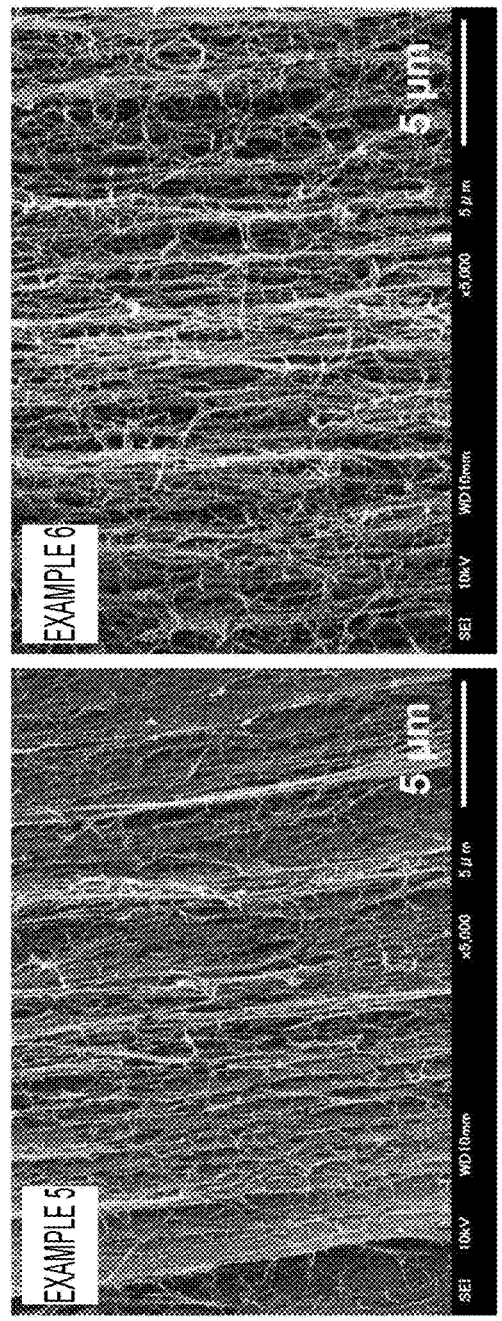
FIG. 9 shows SEM images of the inside of string-like collagen sols produced by changing the inner diameter of the stainless steel tube.

When the collagen sol A that was rapidly converted into fibrils was supplied to a flow path with a predetermined length at a predetermined shear rate as shown in Table 2, since a similar stainless steel tube in which the inner diameter of the stainless steel tube increased from 2 mm to 2.84 mm was used, the same orientation mechanism as in Example 2 was operated and a high collagen fibril orientation was obtained (FIG. 9). When the inner diameter of the stainless steel tube increased, the cross-sectional areas of the string-like collagen gel and dried collagen fibers obtained therefrom increased (FIG. 4). Since the orientation of collagen fibrils inside was high, the Young's modulus in the wet state was significantly larger compared to Comparative Example 2 produced under conditions in which the degree of orientation decreased (FIG. 8D), and the Young's modulus in the dry state and the breaking stress in the dry state and wet state tended to be high (FIGS. 8B, 8D, and 8E). While fibrils of Example 5 were oriented, the breaking strain was the same as in Comparative Example 2 both in the dry state and wet state (FIGS. 8C and 8F). The total length of dried collagen fibrils was 4.2 m, and the total length of gel fibrils was estimated to be 4.2 m.

Example 6

A string-like collagen fibrillar gel was produced and evaluated in the same manner as in Example 1 except that production conditions were changed as shown in Table 2. Dry fibers were produced in the same manner as in Example 2, and a tensile test was performed. The tensile test was not performed on the wet fibers because the fibril diameter was small and drying started while the wet fibers were taken out of PBS and attached to a testing machine.

Evaluation

When the collagen sol A that was rapidly converted into fibrils were supplied to a flow path with a predetermined length at a predetermined shear rate as shown in Table 2, a similar stainless steel tube in which the inner diameter of the stainless steel tube was reduced from 2 mm to 0.9 mm was used, the same orientation mechanism as in Example 2 was operated and a high collagen fibril orientation was obtained (FIG. 9). When the inner diameter of the stainless steel tube was reduced, the cross-sectional areas of the string-like collagen gel and dried collagen fibers obtained therefrom decreased (FIG. 4). Since the orientation of collagen fibrils inside was high, the Young's modulus in the dry state and the breaking stress were significantly larger compared to Comparative Example 2 produced under conditions in which the degree of orientation decreased (FIGS. 8A and 8B). On the other hand, the breaking strain during drying was the same as in Comparative Example 2 (FIG. 8C).

Example 7

Figure 10:
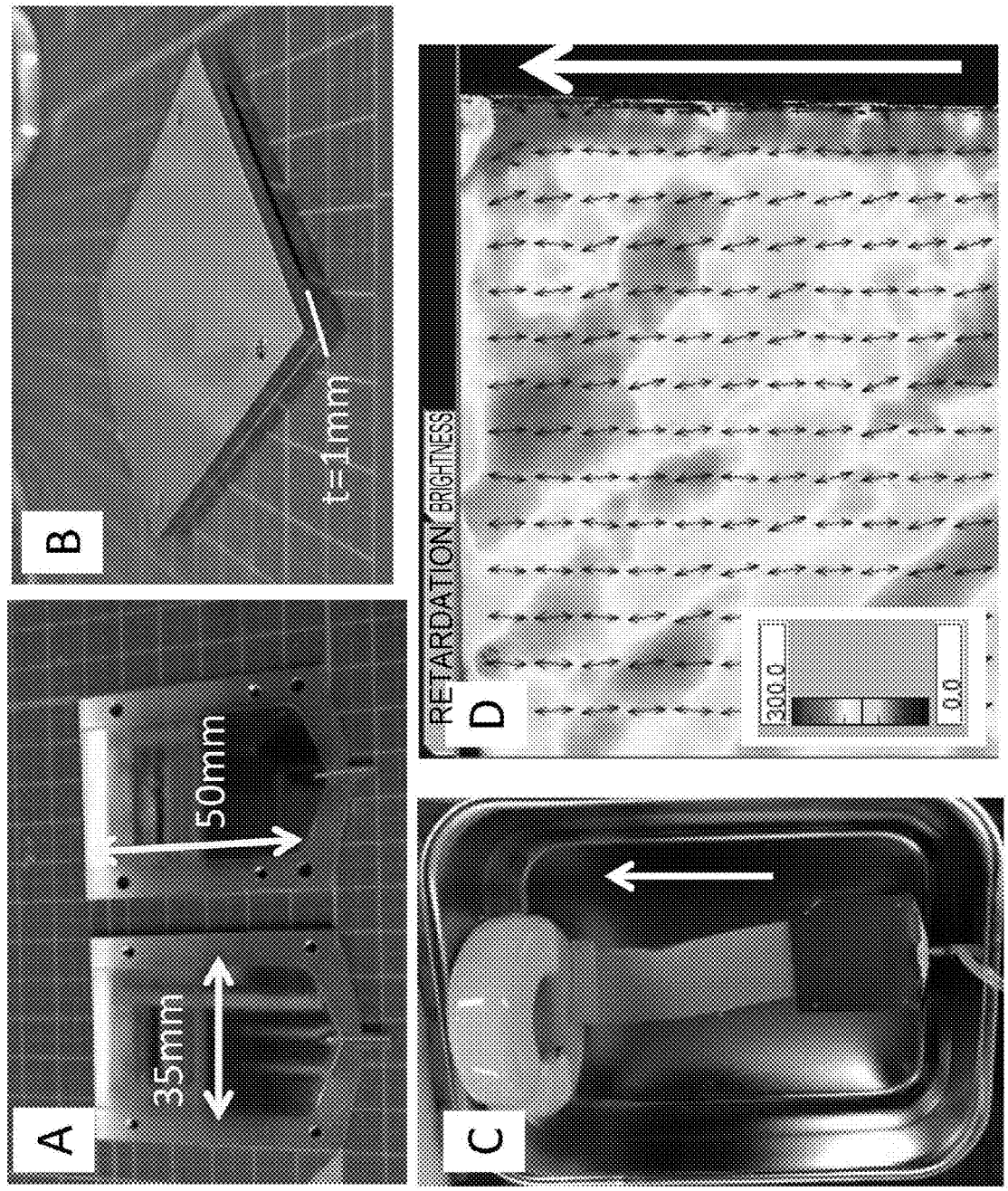
FIG. 10A shows a state of a disassembled T die mold used in Example 7.
FIG. 10B shows the appearance after assembly.
FIG. 10C shows a state of continuous molding of band-like collagen.
FIG. 10D shows a 2D birefringence image of a band-like collagen gel. White arrows in FIGS. 10C and 10D indicate a molding direction of a band-like collagen gel, and small black arrows in FIG. 10D indicate the main axis direction (orientation direction).

A collagen fibrillar gel was produced in the same manner as in Example 1 except that the mold was changed to a T die mold (FIGS. 10A and 10B) from the stainless steel tube and production conditions were changed as shown in Table 2.

Evaluation

The sheet-like collagen gel was continuously spun from a slit of the T die mold (FIG. 10C). The birefringence was measured, but not yet analyzed. The orientation in the molding direction was observed in the 2D birefringence image of the obtained band-like collagen gel (FIG. 10D).

Comparative Example 1

A string-like collagen fibrillar gel was produced and evaluated in the same manner as in Example 1 except that production conditions were changed as shown in Table 2.

Evaluation

Figure 11:
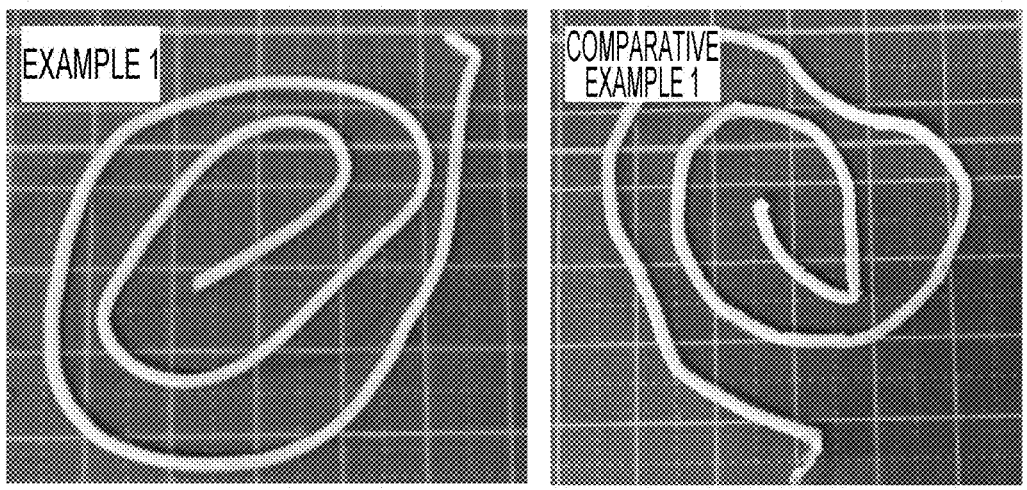
FIG. 11 is a diagram showing the appearances of string-like collagen gels of Example 1 and Comparative Example 1.

Even when the collagen sol A that was rapidly converted into fibrils was supplied to a flow path with a predetermined length as shown in Table 2, if the shear rate exceeded 2 $s^{-1}$, the degree of orientation was high (FIG. 5). However, since a strong frictional force was applied into the stainless steel tube, a string-like collagen gel with a rough surface was obtained (FIG. 11).

Comparative Example 2

A string-like collagen fibrillar gel was produced and evaluated in the same manner as in Example 1 except that production conditions were changed as shown in Table 2.

Evaluation

Figure 12:
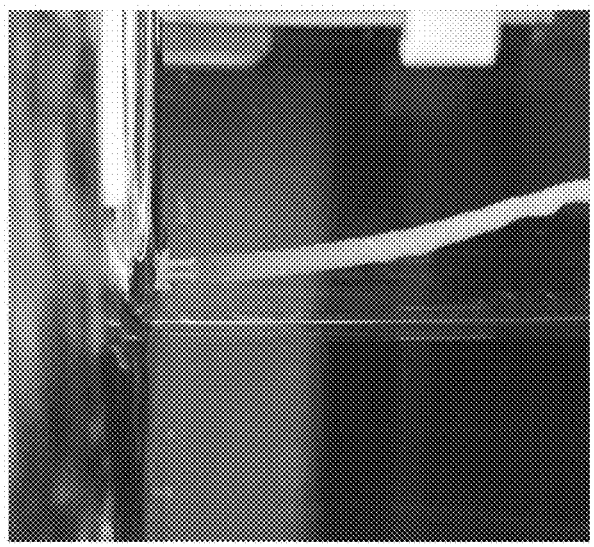
FIG. 12 is a diagram showing the appearance of spinning of Comparative Example 2.

Even when the collagen sol A that was rapidly converted into fibrils was supplied to a flow path at a predetermined shear rate as shown in Table 2, if the flow path length ratio was less than 20%, since sufficient collagen fibrosis and orientation did not proceed until the collagen sol was discharged (FIG. 12), a string-like collagen gel having a low collagen fibril orientation was obtained (FIG. 6).

Comparative Example 3

A string-like collagen fibrillar gel was produced and evaluated in the same manner as in Example 1 except that production conditions were changed as shown in Table 2.

Evaluation

Even when the collagen sol A that was rapidly converted into fibrils was supplied to a flow path with a predetermined length as shown in Table 2, if the shear rate was less than 0.2 $s^{-1}$, since sufficient collagen fibrils were not oriented, a string-like collagen gel having low orientation was obtained (FIGS. 5 and 7).

Comparative Example 4

The collagen sol A was filled into a silicone rubber tube with an inner diameter of 2 mm, an outer diameter of 4 mm, and a length of 1 m, both ends of the tube were clipped, immersion was performed in a water bath at 38.0° C. for 1 hour, and the collagen sol was converted into fibrils. A syringe filled with 2×NPB was connected to one end of the tube, and the gelled collagen was extruded. Then, the collagen was crosslinked as in Example 1 and evaluated.

Evaluation

Even when the collagen sol A2 that was rapidly converted into fibrils was used, since no shear was applied in the flow path, no collagen fibrils were oriented (FIGS. 5 and 7).

Comparative Example 5

A string-like collagen fibrillar gel was produced using the stainless steel tube with the same inner diameter as in Example 1 except that the collagen sol B was used in place of the collagen sol A (Table 1) so that the same shear rate and flow path length ratio were obtained, and the gel was evaluated.

Evaluation

Figure 13:
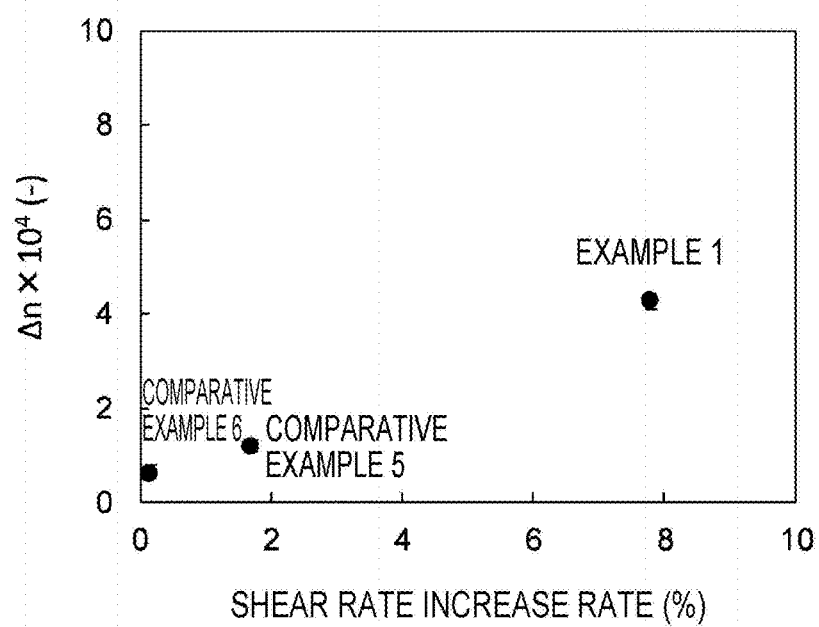
FIG. 13 is a diagram showing the relationship between a shear rate increase rate and a refractive index difference $\Delta n$.

The shear stress increase rate of the collagen sol B was less than 2%, and fibrosis was slower than that of the collagen sol A. When such a collagen sol was used, even if the sol was supplied to a flow path with an appropriate length at an appropriate shear rate, since simultaneous progressing of fibrosis and orientation did not appropriately proceed, a string-like collagen gel having a refractive index difference reduced to 1.17±0.10 was obtained (FIG. 13).

Comparative Example 6

A string-like collagen fibrillar gel was produced using the stainless steel tube with the same inner diameter and the same shear rate as in Example 1 except that the collagen sol C was used in place of the collagen sol A (Table 1), and the gel was evaluated.

Evaluation

The shear stress increase rate of the collagen sol C was less than 2%, and fibrosis was slower than that of the collagen sol A. When such a collagen sol was used, even if the sol was supplied to a flow path with an appropriate length at an appropriate shear rate, since simultaneous progressing of fibrosis and orientation did not appropriately proceed, a string-like collagen gel having a refractive index difference reduced to 0.59±0.06 was obtained (FIG. 13). The forms of fibrils observed according to SEM observation were almost disordered as in Comparative Example 4 produced without shear application (FIG. 7). Since collagen fibrils inside were unlikely to be oriented, as described in detail in Example 2, compared to Example 2 produced under conditions in which the degree of orientation increased, tensile properties deteriorated both in the dry state and wet state (FIG. 8).

Comparative Example 7

Wet spinning was performed. An acidic collagen aqueous solution with a concentration of 2.5% was accommodated into a Terumo syringe with a capacity of 30 mL, which was connected to a stainless steel tube (φ2.00 mm×26.3 mm) via a 25 cm silicone rubber tube. Only the stainless steel tube was immersed in 1×NPB (containing 20% PEG-8000) accommodated in a stainless steel container warmed to a range of 37.5° C. to 37.9° C. in a water bath, and the collagen sol was sent at a constant rate (14.1·h$^{-1}$) using a syringe pump. Since the discharged collagen aqueous solution was very hard to solidify and integrated to each other, spinning continued while adjusting the flow direction with a bamboo skewer. Then, the collagen was crosslinked in the same manner as in Example 1, and evaluated.

Evaluation

Figure 14:
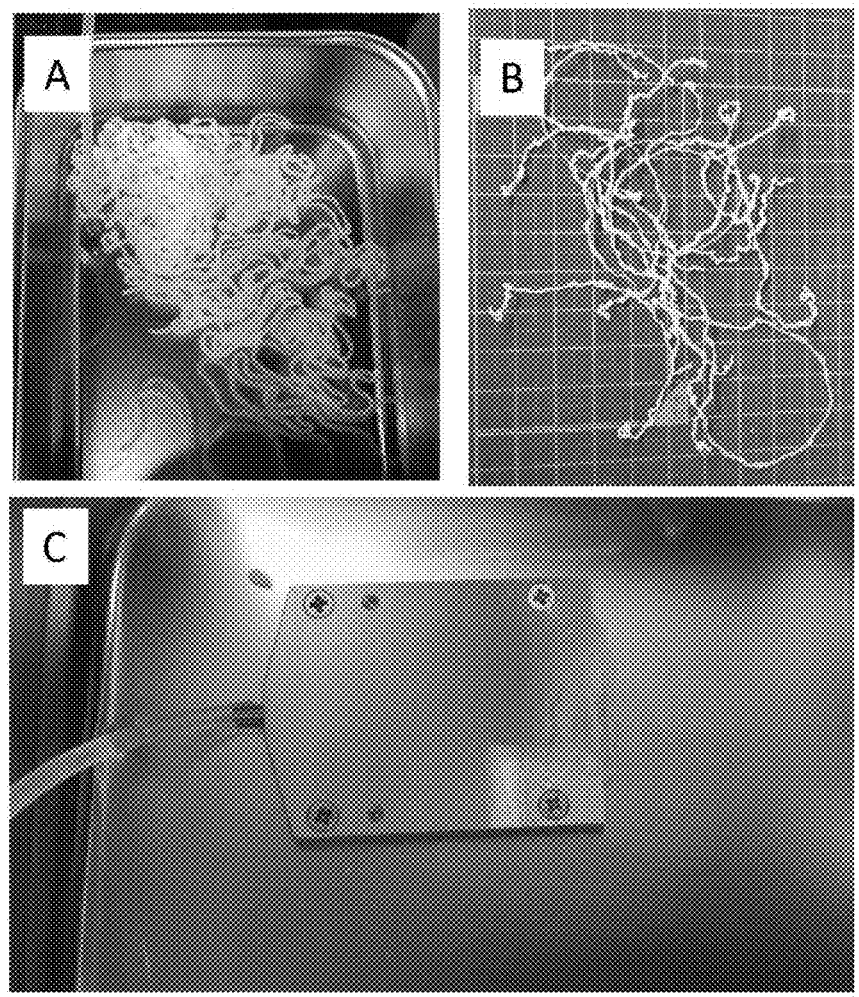
FIG. 14A shows the state of wet spinning (Comparative Example 7)
FIG. 14B shows the appearance of fibers obtained by drying the string-like collagen gel obtained by wet spinning.
FIG. 14C shows a procedure of producing a band-like collagen gel using a T die mold according to a wet spinning principle (Comparative Example 8).

When a medical collagen aqueous solution was discharged from a stainless steel tube with an inner diameter of 2 mm using conventional wet spinning, coagulation takes time due to slow fibrosis, and cutting was performed in some points and a curly string-like collagen gel was obtained in some cases (FIG. 14A), and long and uniform collagen fibrils were not obtained even when dried (FIG. 14B). The total length of the string-like collagen gel was 0.7 m at maximum.

Comparative Example 8

A collagen aqueous solution was discharged from a mold in the same manner as in Comparative Example 7 except that the mold was changed to a T die mold (FIG. 10) from the stainless steel tube, and the aqueous solution became beads at the outlet of the mold and uniform molding was not possible (FIG. 14C).

INDUSTRIAL APPLICABILITY

According to the present invention, it is possible to provide a collagen fibril bundle highly oriented in a uniaxial direction that can be used for medical collagen gels and a collagen gel which contains the same and has a desired shape depending on the purpose. Therefore, the collagen fibril bundle and the collagen gel containing the same of the present invention are expected to be applied to various biomaterials.

What is claimed is:

1. A uniaxially oriented collagen fibril bundle having a total length in a major axis direction of 1 m or more, wherein from the surface to the inside, the bundle has a refractive index difference Δn of $3\times10^{-4}$ to $10^{-2}$.

2. The collagen fibril bundle according to claim 1, wherein from the surface to the inside, the bundle has the refractive index difference Δn of $3\times10^{-4}$ to $10^{-2}$ at multiple points along the length of the collagen fibril bundle.

3. A collagen gel containing the collagen fibril bundle according to claim 1.

4. The collagen gel according to claim 3, which is molded into a string or band shape.

5. The collagen gel according to claim 4, wherein the collagen gel has a string form and has a diameter of 0.2 mm or more.

6. The collagen gel according to claim 3, wherein the collagen gel has a cross-sectional area in a range of $3\times10^{-2}$ mm$^2$ to 700 mm$^2$.

7. The collagen gel according to claim 3, wherein the refractive index difference Δn is measured according to birefringence measurement at the point of production of the collagen gel.

8. A dried component of the collagen gel according to claim 3.

9. A method of producing a collagen gel comprising a uniaxially oriented collagen fibril bundle, said bundle having a total length in a major axis direction of 1 m or more and, from the surface to the inside, a refractive index difference Δn of $3\times10^{-4}$ to $10^{-2}$, the method comprising
continuously introducing a collagen sol into a flow channel maintained at a temperature in a range of 30° C. to 50° C.,
increasing the shear stress on the collagen sol in the flow channel at a rate of 2% to 40% per second for 2 seconds to 120 seconds, and
discharging the collagen gel from the flow channel.

10. The method according to claim 9, wherein a collagen concentration of the collagen sol is 1.0 mass % to 10 mass %.

11. The method according to claim 9, wherein the flow channel has a cylindrical flow path having a circular or elliptical cross section, and a ratio L/R of a linear velocity L (mm·s$^{-1}$) of a flow rate of the collagen gel to the diameter or minor axis diameter R (mm) of the cross section is in a range of 0.2 to 2 (s$^{-1}$).

12. The method according to claim 9, wherein the flow channel has a cylindrical flow path having a rectangular cross section, and a ratio L/X of a linear velocity L (mm·s$^{-1}$) of a flow rate of the collagen gel to a short side X (mm) of the cross section is in a range of 0.2 to 2 (s$^{-1}$).

13. The method according to claim 9, wherein, when the flow channel has a cylindrical flow path having a circular or elliptical cross section, the diameter or minor axis diameter of the cross section is R (mm), and when the flow channel has a cylindrical flow path having a rectangular cross section, a short side of the cross section is X (mm), and when a time to reach a maximum value or plateau value of the shear stress obtained according to rotation shear stress measurement on the collagen sol using a parallel plate type rheometer in which a sensor gap is set to R/2 (mm) or X/2 (mm), and a sensor temperature is set to an insulation temperature of the flow path is Tau-max(s), the flow path has a flow path length of 20% to 400% of a length calculated by a product of the linear velocity L (mm·s$^{-1}$) of the collagen sol and Tau-max.

\* \* \* \* \*